US010731146B2

United States Patent
Vlassov et al.

(10) Patent No.: US 10,731,146 B2
(45) Date of Patent: Aug. 4, 2020

(54) PURIFICATION OF NUCLEIC ACID FROM ENVIRONMENTAL OR BIOLOGICAL SAMPLES

(71) Applicant: Life Technologies Corporation, Carlsbad, CA (US)

(72) Inventors: Alexander Vlassov, Carlsbad, CA (US); Sarah Larocca, Austin, TX (US); Mu Li, San Diego, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 15/909,789

(22) Filed: Mar. 1, 2018

(65) Prior Publication Data

US 2018/0195057 A1  Jul. 12, 2018

Related U.S. Application Data

(63) Continuation of application No. PCT/US2016/051075, filed on Sep. 6, 2016.

(60) Provisional application No. 62/216,676, filed on Sep. 10, 2015.

(51) Int. Cl.
| | | |
|---|---|---|
| C12P 19/34 | (2006.01) | |
| C12N 15/10 | (2006.01) | |
| C12Q 1/6806 | (2018.01) | |
| G01N 33/569 | (2006.01) | |
| G01N 33/574 | (2006.01) | |
| C12Q 1/686 | (2018.01) | |

(52) U.S. Cl.
CPC ....... *C12N 15/1003* (2013.01); *C12Q 1/6806* (2013.01); *G01N 33/56938* (2013.01); *G01N 33/574* (2013.01); *C12Q 1/686* (2013.01); *G01N 2800/06* (2013.01)

(58) Field of Classification Search
None
See application file for complete search history.

(56) References Cited

U.S. PATENT DOCUMENTS

| | | | |
|---|---|---|---|
| 6,037,465 A | 3/2000 | Hillebrand et al. | |
| 6,084,091 A | 7/2000 | Muller et al. | |
| 6,177,278 B1 | 1/2001 | Haj-Ahmad | |
| 6,291,248 B1 | 9/2001 | Haj-Ahmad | |
| 7,459,548 B2 | 12/2008 | Brolaski et al. | |
| 7,790,865 B1 | 9/2010 | Heath et al. | |
| 2005/0282202 A1 | 12/2005 | Brolaski et al. | |
| 2006/0088849 A1* | 4/2006 | Happe | C12Q 1/689 435/6.11 |
| 2011/0201022 A1* | 8/2011 | Foehr | G01N 33/573 435/7.4 |
| 2011/0296747 A1 | 12/2011 | Sonomoto et al. | |
| 2014/0363400 A1 | 12/2014 | Jones et al. | |

FOREIGN PATENT DOCUMENTS

| | | |
|---|---|---|
| CN | 101205621 | 6/2008 |
| EP | 0765335 | 4/1997 |
| EP | 0851937 | 7/1998 |
| EP | 1756136 | 2/2007 |
| KR | 2005-0003114 | 1/2005 |
| RU | 2092885 | 10/1997 |
| WO | 1997/013496 | 4/1997 |
| WO | WO-2012089729 | 7/2012 |
| WO | 2017/044827 | 3/2017 |

OTHER PUBLICATIONS

Anonymous, "Determination of Aqueous [FeII] & [FeIII] with Ferrozine", *UCI Faculty Websites*, http://faculty.sites.uci.edu/chem21/files/2014/03/Week2LabProcVISFerrozine-SAA-DMF.pdf, Jul. 4, 2014, 1-4.

Braid et al., "Removal of PCR Inhibitors from soil DNA by chemical flocculation", *Journal of Microbiological Methods*, vol. 52, No. 3, Mar. 1, 2003, 389-393.

Conrad et al., "The Human Microbiota: Composition, Functions, and Therapeutic Potential", *Medical Science Review*, vol. 2, 2015, 92-103.

Dijkmans et al., "Rapid method for purification of soil DNA for hybridization and PCR analysis", *Microbial Releases*, vol. 2, No. 1, 29-34, Jun. 1, 1993.

Lever et al., "A modular method for the extraction of DNA and RNA, the separation of DNA pools from diverse environmental sample types", *Frontiers in Microbiology*, vol. 6, No. 476, May 15, 2015, 1-25.

Mackenzie et al., "Evaluating variation in human gut microbiota profiles due to DNA extraction method and inter-subject differences", *Frontiers in Microbiology*, vol. 6, Feb. 2015, 1-11.

MIOBIO LaboratoriesInc., "PowerFecal DNA Isolation Kit", *Instructions Manual*, Catalog No. 12830-50, 2013, 1-16.

MOBIO Laboratories, Inc., "PowerSoil DNA Isolation Kit", *Instruction Manual*, Catalog Nos. 12888-50 and 12888-100, 2013, 1-16.

PCT/US2016/051075, International Search Report and Written Opinion, dated Feb. 17, 2017, 1-14.

PCT/US2016/051075, International Preliminary Report on Patentability, dated Mar. 22, 2018, 1-8.

* cited by examiner

*Primary Examiner* — James Martinell

(57) ABSTRACT

Compositions and methods for nucleic acid isolation from an environmental or biological sample comprising nucleic acid-analysis interferents, particularly from microbiome-containing samples, are provided.

19 Claims, 18 Drawing Sheets

Specification includes a Sequence Listing.

| | D12-1 | D12-2 | D12-3 | D13-1 | D13-2 | D13-3 |
|---|---|---|---|---|---|---|
| Bacteroides | 20.26677 | 21.89926 | 24.76608 | 27.01573 | 20.20705 | 30.30062 |
| Faecalibacterium | 25.82122 | 21.68027 | 28.8473 | 21.50109 | 20.06769 | 21.44137 |
| Sutterella | 5.355365 | 7.007764 | 6.868405 | 0 | 0 | 0 |
| Coprococcus | 3.523791 | 3.384432 | 2.428827 | 0.278718 | 0.457894 | 0.238901 |
| Streptococcus | 2.050567 | 2.249652 | 1.592674 | 0.099542 | 0.139359 | 0.139359 |
| Clostridium | 2.030659 | 2.826996 | 2.667728 | 0.398168 | 0.318535 | 0.258809 |
| Roseburia | 0.497711 | 0.298626 | 0.437985 | 1.13478 | 1.294047 | 1.114872 |
| Lachnospira | 2.010751 | 3.40434 | 2.070476 | 4.220585 | 5.415091 | 5.514633 |
| Subdoligranulum | 0 | 0 | 0 | 3.583516 | 2.727454 | 3.961776 |
| Ruminococcus | 0 | 0 | 0 | 2.010751 | 2.329285 | 1.970934 |
| Pseudobutyrivibrio | 5.912801 | 6.171611 | 5.494724 | 18.913 | 21.44137 | 13.67709 |
| Other | 32.53036 | 31.07705 | 24.8258 | 20.84412 | 25.60223 | 21.38164 |

FIG. 6

```
                              SEQUENCE LISTING

<160> NUMBER OF SEQ ID NOS: 9

<210> SEQ ID NO 1
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
gcgtgcttaa cacatgcaag tc                                                  22

<210> SEQ ID NO 2
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
catccggcat taccacccgt t                                                   21

<210> SEQ ID NO 3
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 3
tcacgcatta ctcacccgtt cgcc                                                24

<210> SEQ ID NO 4
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
catgccgcgt gtatgaagaa                                                     20

<210> SEQ ID NO 5
<211> LENGTH: 21
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic primer"

<400> SEQUENCE: 5
cgggtaacgt caatgagcaa a                                               21

<210> SEQ ID NO 6
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 6
tattaacttt actcccttcc tccccgctga a                                    31

<210> SEQ ID NO 7
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
cctacgatgg atagggg tt                                                 19

<210> SEQ ID NO 8
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
cacgctactt ggctggttca g                                               21

<210> SEQ ID NO 9
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 9
aaggtccccc acattg                                                     16
```

PURIFICATION OF NUCLEIC ACID FROM ENVIRONMENTAL OR BIOLOGICAL SAMPLES

CROSS REFERENCE

This application is a continuation application under 35 U.S.C. § 120 of pending International Application No. PCT/US2016/051075 filed Sep. 9, 2016 which application claims the benefit under 35 U.S.C. § 119(e) of U.S. Provisional Application No. 62/216,676 filed Sep. 10, 2015. The entire contents of the aforementioned applications are incorporated herein.

SEQUENCE LISTING

The instant application contains a Sequence Listing which has been submitted electronically in ASCII format and is hereby incorporated by reference in its entirety. Said ASCII copy, created on Nov. 23, 2016, is named LT01075PCT_SL.txt and is 2,539 bytes in size.

FIELD

The present teachings generally relate to compositions, methods, and kits for purification of nucleic acid for detection, quantitation and/or analysis from environmental or biological samples, particularly microbiome containing samples.

INTRODUCTION

Environmental samples containing microbial flora can present challenges for nucleic acid analysis therefrom primarily due to the presence of compounds that interfere with later analytic techniques such as the polymerase chain reaction (PCR or qPCR) or reverse transcriptase PCR (RT PCR). Humic substances are an example of a PCR-interferent that co-purifies with nucleic acid and are abundant in environmental samples, particularly in soil samples. Braid et al. (*J of Microbiological Methods* 52 (2003) 389-393) used solutions of each of the flocculants, magnesium chloride, ferric chloride, calcium chloride, and aluminum ammonium sulfate to remove soil-based inhibitors from environmental DNA and reportedly found that the aluminum ammonium sulfate significantly reduced the co-purification of PCR inhibitors with minimal loss of DNA yield.

The human body is populated by 100 trillion bacteria, viruses, fungi and other members of the microbiota family that play a fundamental role in our well-being. Deviations from healthy microbial compositions in the GI tract, skin, oral or urogenital areas have been linked with human disease such as inflammatory bowel disease, obesity, cancer, asthma, diabetes and allergies. Although our understanding of the microbiome and its interaction with the host is in its infancy, it has become increasingly clear that we need to treat it as a sophisticated system, much like the circulatory system or the immune system, existing in homeostasis within the human body.

Thus, efficient and effective fundamental research tools and reagents are highly desired to ensure accurate characterization of the composition of microbial communities, to study interdependent function within a microbial community, and to allow manipulation of interactions within a microbial community as well as between a microbial community and its host. Next generation tools such as improved kits for isolation of microbial nucleic acid, for sequencing, and for data analysis are urgently required.

Kits currently available on the market for isolating DNA from environmental samples and biological samples include the MO BIO PowerSoil® DNA Isolation Kit and the PowerFecal™ DNA Isolation Kit (MO BIO Laboratories, Inc. Carlsbad Calif.). Instruction manuals for each kit indicate that the kits provide for removal of non-DNA material from samples using an Inhibitor Removal Technology® method (IRT) that includes two separate steps of inhibitor removal interrupted by a centrifugation. IRT is cited as relating to U.S. Pat. No. 7,459,548, which patent granted to Brolaski et al. Dec. 2, 2008 and which sets forth a method of using flocculation at a critical stage in the removal of inhibitory material. In a first step, a sample is contacted with, inter alia, a detergent and a first flocculant (ammonium acetate) and the precipitate is separated from the nucleic acid before the nucleic acid is contacted with a second flocculant (aluminum ammonium sulfate dodecahydrate) in a second step.

The embodiments described below provide nucleic acid preparation methods and reagents that allow for simplified and more effective removal of interferents from microbiome-containing samples such that resultant purified nucleic acid is not hampered by the presence of those interferents in subsequent analyses.

SUMMARY

A "microbiome" as used herein refers to an ecological community of microorganisms present in an environment or in a biological system. An environmental sample or a sample from a biological system may comprise, for example, a sample derived from an animal, food, a plant or a component thereof, soil, sediment, sludge, compost, decomposing biological matter, a biopsy, a histological sample, a body fluid or swab thereof, hair, a skin sample or swab thereof, a fecal sample or swab thereof, archaeological remains, a peat bog, a water filter or swab thereof, terrestrial water, subterranean water, industrial water or filter thereof, a dust filter or swab thereof, transport media, culture media, or an air filter or swab thereof. The environmental or biological sample may comprise a soil sample or a fecal (stool) sample.

Experimental studies provided herein demonstrate that interferents of nucleic acid analyses that are present in an environmental microbiome-containing sample or a biological microbiome-containing sample are readily removed in a single precipitation step carried out on a cell lysate or cell lysate supernatant of that sample. The resulting interferent-depleted supernatant can be directly assayed in nucleic acid analyses methods or taken through standard nucleic acid purification protocols.

As used herein, the term "interferent" refers to any chemical or physical substance that can interfere with or disrupt a reaction or process involving DNA or RNA and includes a contaminant or an inhibitor that has a detrimental effect on DNA or RNA manipulation. Examples of an interferent include an inhibitor of an enzymatic reaction that uses DNA or RNA as a substrate and a contaminant that disrupts hybridization of DNA or RNA, for example. An interferent may be a chitin, decomposing plant material, an enzymatic inhibitor from soil, a humic substance such as humic acid, a humic polymer, humin, humates, or fulvic acid, an organic compound from compost, a phenolic, a phenolic polymer or oligomer, a photosynthetic pigment, a plant cell wall, a plant pigment, polyphenol, a polysaccharide, or a tannin, for example.

An embodiment as presented herein is a composition comprising ammonium acetate and either aluminum ammonium sulfate, ammonium sulfate dodecahydrate, aluminum ammonium sulfate dodecahydrate, aluminum potassium sulfate, aluminum chlorohydrate, aluminum sulfate, calcium oxide, iron (III) chloride, iron (II) sulfate, sodium aluminate, sodium silicate, or a combination thereof.

An embodiment also as presented herein is a composition comprising ammonium acetate and a flocculant, wherein the flocculant is aluminum ammonium sulfate, ammonium sulfate dodecahydrate, aluminum ammonium sulfate dodecahydrate, aluminum potassium sulfate, aluminum chlorohydrate, aluminum sulfate, calcium oxide, iron (III) chloride, iron (II) sulfate, sodium aluminate, sodium silicate, or a combination thereof. In one embodiment, the composition comprises ammonium acetate and a flocculant, wherein the flocculant is aluminum ammonium sulfate or aluminum ammonium sulfate dodecahydrate. In a further embodiment, the composition comprises ammonium acetate, a flocculant, and either a cell lysate, a volume portion thereof, a supernatant thereof, or a volume portion of supernatant thereof.

Stock solutions of the composition may comprise ammonium acetate and flocculant, each in a concentration of 5 mM, 10 mM, 50 mM, 100 mM, 0.2 M, 0.3 M, 0.4 M, 0.5 M, 1 M, 5 M, or 10 M or any integer or decimal value there between or any integer or decimal range there between. The concentration of each of the ammonium acetate and the flocculant may be the same or may be different. In an embodiment, the composition comprises a solution of ammonium acetate and aluminum ammonium sulfate dodecahydrate, and in a further embodiment, each is present in substantially equimolar concentrations. As used herein, the term "substantially equimolar" refers to a concentration of ammonium acetate that is about equal to the concentration of flocculant ±30% as measured in moles per liter. Another embodiment is a composition consisting of a solution of ammonium acetate and a flocculant, such as aluminum ammonium sulfate dodecahydrate, in substantially equimolar concentrations.

In an embodiment of the composition described above, the composition comprises a solution of 5 mM to 300 mM ammonium acetate and 5 mM to 300 mM flocculant, a solution of 5 mM to 200 mM ammonium acetate and 5 mM to 200 mM flocculant, a solution of 25 mM to 200 mM ammonium acetate and 25 mM to 200 mM flocculant, a solution of 50 mM to 150 mM ammonium acetate and 50 mM to 150 mM flocculant, a solution of 50 mM to 130 mM ammonium acetate and 50 mM to 130 mM flocculant. In one instance, the composition comprises a solution of 175 mM ammonium acetate and 175 mM flocculant in substantially equimolar amounts, a solution of 150 mM ammonium acetate and 150 mM flocculant in substantially equimolar amounts, or a solution of 130 mM ammonium acetate and 130 mM flocculant in substantially equimolar amounts. In one instance, the composition comprises a solution of 65 mM ammonium acetate and 65 mM flocculant in substantially equimolar amounts. In one instance, the composition comprises a solution of 50 mM ammonium acetate and 50 mM flocculant in substantially equimolar amounts.

In a further embodiment, the composition comprises a mixture of ammonium acetate and a flocculant as solid ingredients, i.e., as a powder or as a salt in, e.g., the form of a tablet. The flocculant comprises aluminum ammonium sulfate, ammonium sulfate dodecahydrate, aluminum ammonium sulfate dodecahydrate, aluminum potassium sulfate, aluminum chlorohydrate, aluminum sulfate, calcium oxide, iron (III) chloride, iron (II) sulfate, sodium aluminate, sodium silicate, or a combination thereof. In one embodiment, the flocculant consists of aluminum ammonium sulfate, ammonium sulfate dodecahydrate, aluminum ammonium sulfate dodecahydrate, aluminum potassium sulfate, aluminum chlorohydrate, aluminum sulfate, calcium oxide, iron (III) chloride, iron (II) sulfate, sodium aluminate, sodium silicate, or a combination thereof. In one embodiment, the flocculant is aluminum ammonium sulfate or aluminum ammonium sulfate dodecahydrate.

A method for isolating a nucleic acid from an environmental or biological sample comprising the nucleic acid and at least one nucleic acid analysis-interferent is an embodiment provided herein. An embodiment of the method comprises a) disrupting the sample using mechanical agitation, enzymatic treatment, chemical treatment, heat treatment, or a combination thereof to produce a lysate; and b) contacting the lysate, a volume portion thereof, a supernatant thereof, or a volume portion of supernatant thereof, with the composition as described above to form an interferent-containing precipitate and a nucleic acid-containing, interferent-depleted solution; and c) isolating nucleic acid from the nucleic acid-containing interferent-depleted solution to form isolated nucleic acid.

A method for isolating DNA from an environmental or biological sample is an embodiment provided herein wherein the sample comprises DNA and DNA analysis-interferents. One embodiment of the method comprises a) disrupting the sample using mechanical agitation, enzymatic treatment, chemical treatment, heat treatment, or a combination thereof to produce a lysate; and b) contacting the lysate, a volume portion thereof, a supernatant thereof, or a volume portion of supernatant thereof, with the composition as described above to form an interferent-containing precipitate and a DNA-containing, interferent-depleted solution; and c) isolating DNA from the DNA-containing interferent-depleted solution to form isolated DNA.

In one aspect of the method, disrupting the sample comprises chemical treatment in the presence of a lysis agent comprising at least one chaotropic agent. Optionally, the lysis agent may comprise a detergent. In one embodiment, the lysis agent does not contain ammonium acetate, sodium chloride, ammonium sulfate, potassium acetate or sodium acetate. In an embodiment, the lysis agent comprises a phosphate buffer. In another embodiment, the disrupting comprises chemical treatment and mechanical treatment in the form of bead beating. In a further embodiment, the disrupting comprises a heating step at, e.g., 65° C. or up to 95° C. for 5 to 10 minutes. In an embodiment, disrupting the sample comprises chemical treatment, mechanical treatment and heat treatment to produce a lysate.

In one aspect, the lysis agent does not contain ammonium acetate, sodium chloride, ammonium sulfate, potassium acetate or sodium acetate.

In an aspect of the method, the composition used in the contacting step comprises a single solution comprising ammonium acetate and a flocculant to form an interferent-containing precipitate and a nucleic acid-containing, interferent-depleted solution. In another aspect, the ammonium acetate and the flocculant are added separately but so close together in time to be effectively added together, i.e., no centrifugation step interrupts the separate additions and no more than five minutes separates the timing of the additions. In another aspect of the method, a solution of ammonium acetate is added in the contacting step followed within two to three minutes by addition of a solution of flocculant. No centrifugation or separation step interrupts the addition steps.

In an embodiment, the composition used in the contacting step is in solid form comprising a mixture of ammonium acetate and a flocculant such that, when contacted with the lysate, a volume portion thereof, a supernatant thereof, or a volume portion of supernatant thereof, provides a final concentration of substantially equimolar amounts. In another aspect, the solid ammonium acetate and the solid flocculant are added separately but so close together in time to be effectively added together, i.e., no centrifugation step interrupts the separate additions and no more than five minutes separates the timing of the additions. In another aspect of the method, the solid form of ammonium acetate is added in the contacting step followed within two to three minutes by addition of the solid form of flocculant. No centrifugation or separation step interrupts the addition steps.

In an aspect wherein the nucleic acid comprises DNA, the method may further comprise d) contacting the isolated DNA with an enzyme utilizing DNA as a substrate. The enzyme may be a polymerase, a ligase, a phosphatase, a kinase, or an enzymatically active fragment or mutant thereof.

A method for removing a DNA analysis-interferent from an environmental or biological sample to produce isolated DNA is an embodiment herein, the method comprising a) disrupting the sample in the presence of a lysis agent comprising detergent and at least one chaotropic agent to produce a lysate, wherein the lysis agent does not contain ammonium acetate, sodium chloride, ammonium sulfate, potassium acetate or sodium acetate; and b) contacting the lysate, a volume portion thereof, a supernatant thereof, or a volume portion of supernatant thereof, with a composition comprising ammonium acetate and a flocculant to form an interferent-containing precipitate and a DNA-containing interferent-depleted solution; and c) isolating DNA from the DNA-containing interferent-depleted solution to produce isolated DNA.

Another embodiment herein is a method for removing or depleting a DNA analysis-interferent from a lysed environmental or biological sample, the improvement comprising: contacting a DNA-containing supernatant of the lysed sample with a composition comprising ammonium acetate and a flocculant to form a precipitate of the DNA analysis-interferent and an interferent-depleted solution comprising DNA.

In another aspect of the method, the isolated DNA may be used in downstream nucleic acid detection methods such as polymerase chain reaction, qPCR, melt curve analysis, linear amplification for array analysis, and other methods that use CYANINE™ 3 or CYANINE™ 5 in array analysis, for example. The isolated DNA may be used in sequencing, genotyping analysis, pathogen analysis, microbial genotyping, gene expression analysis, copy number analysis, DNA methylation analysis, or SNP genotyping, for example.

In another aspect of the method, the biological sample is a stool sample and the isolated DNA is assayed for DNA characteristic of a pathogenic organism such as, e.g., *C. difficile*, methicillin-resistant *Staphylococcus aureus*, or a vancomycin-resistant *enterococcus*, or a virus such as rotavirus, norovirus, cytomegalovirus, herpes simplex virus or hepatitis virus.

In an embodiment herein, the isolated DNA is characterized by sequencing at least a portion of the isolated DNA to generate resultant sequences. In one embodiment, the biological sample is a stool sample and the method further comprises comparing resultant sequences with a control set of sequences representing a healthy microbiome, thereby e.g., determining suitability of the stool sample for transplantation into a patient in need of a healthy gut microbiome, or determining presence of abnormal cells such as cancer cells, particularly colon cancer cells. In another embodiment, the biological sample is a forensic sample and the method further comprises comparing resultant sequences with a control set of sequences representing a forensic data set, thereby identifying e.g., a source of the sample, or degree of decay of a host source of the sample, thereby providing an estimated time of death of a host source of the sample.

A method for removing an assay inhibitor from a crude sample preparation comprising nucleic acid is an aspect of embodiments herein, the method comprising contacting the crude sample preparation with ammonium acetate and a flocculant under conditions wherein the assay inhibitor forms a precipitated complex, and separating the precipitated complex from the crude sample preparation to produce a clarified sample preparation comprising nucleic acid. In an aspect of the method, the crude sample preparation is a supernatant prepared from a stool sample.

A method for isolating RNA from an environmental or biological sample comprising RNA and RNA analysis-interferents is an aspect herein. The method comprises contacting the sample with a RNA stabilization reagent, disrupting the sample using mechanical agitation, enzymatic treatment, chemical treatment, heat treatment, or a combination thereof to produce a lysate, contacting the lysate, a volume portion thereof, a supernatant thereof, or a volume portion of supernatant thereof, with the above described composition to form an interferent-containing precipitate and a RNA-containing, interferent-depleted solution, and isolating RNA from the RNA-containing interferent-depleted solution to form isolated RNA. In an embodiment, a deoxyribonuclease may be added at the contacting step, the disrupting step, the interferent removal step or the isolating step to form isolated RNA.

Embodiments herein also include kit for isolating DNA or RNA from an environmental or biological sample, comprising, singly or in combination: a disrupting reagent, and a composition comprising ammonium acetate and a flocculant, wherein the flocculant is aluminum ammonium sulfate, ammonium sulfate dodecahydrate, aluminum ammonium sulfate dodecahydrate, aluminum potassium sulfate, aluminum chlorohydrate, aluminum sulfate, calcium oxide, iron (III) chloride, iron (II) sulfate, sodium aluminate, sodium silicate, or a combination thereof.

The kit may further comprise a polymerase, nucleotides for PCR amplification, a reverse primer, a forward primer, a TAQMAN™ probe, or a combination thereof. The polymerase may be a DNA polymerase, a RNA polymerase or an enzymatically active fragment or mutant thereof. In an embodiment of the kit, the flocculant is aluminum ammonium sulfate dodecahydrate, and the composition comprises substantially equimolar concentrations of ammonium acetate and aluminum ammonium sulfate dodecahydrate.

For RNA isolation, the kit may include a collection tube containing therein a stabilization reagent, such as, e.g., the RNAlater™ Stabilization Solution (Thermo Fisher Scientific, Cat No. AM7021). The kit may include a reverse transcriptase or an enzymatically active fragment or mutant thereof. The kit may include a DNase or an enzymatically active fragment or mutant thereof.

The composition, methods and kits provided herein provide for a superior combination of nucleic acid yield, nucleic acid purity, effective amplification and short workflow time for a variety of environmental and biological samples containing nucleic acid analysis interferents. These and other features of the present teachings will become more apparent from the description herein.

BRIEF DESCRIPTION OF THE DRAWINGS

The skilled artisan will understand that the drawings, described below, are for illustration purposes only. The drawings are not intended to limit the scope of the present teachings in any way. For each set of data, DNA isolation was carried out from the same stool or soil sample derived from one source, in triplicate.

For the data of FIG. 1A-FIG. 1C and FIG. 2A-FIG. 2C, the interferent removal conditions tested were as follows (i.e., the concentration of ammonium acetate and/or flocculant present in the contacting step with lysate, a volume portion thereof, a supernatant thereof, or a volume portion of supernatant thereof):

a) 25 mM ammonium acetate;
b) 50 mM ammonium acetate;
c) 25 mM flocculant;
d) 50 mM flocculant;
e) 25 mM ammonium acetate;
f) a solution of 25 mM ammonium acetate and 25 mM flocculant;
g) a solution of 50 mM ammonium acetate and 50 mM flocculant;
h) 25 mM ammonium acetate, then subsequent treatment with 25 mM flocculant; and
i) 25 mM flocculant, then subsequent treatment with 25 mM ammonium acetate.

For the data of FIG. 2C, FIG. 3C, FIG. 4C, and FIG. 5C, M refers to the TrackIt™ 1 Kb Plus DNA Ladder (Thermo Fisher Scientific, Cat No. 10488-085).

Figure 1A:
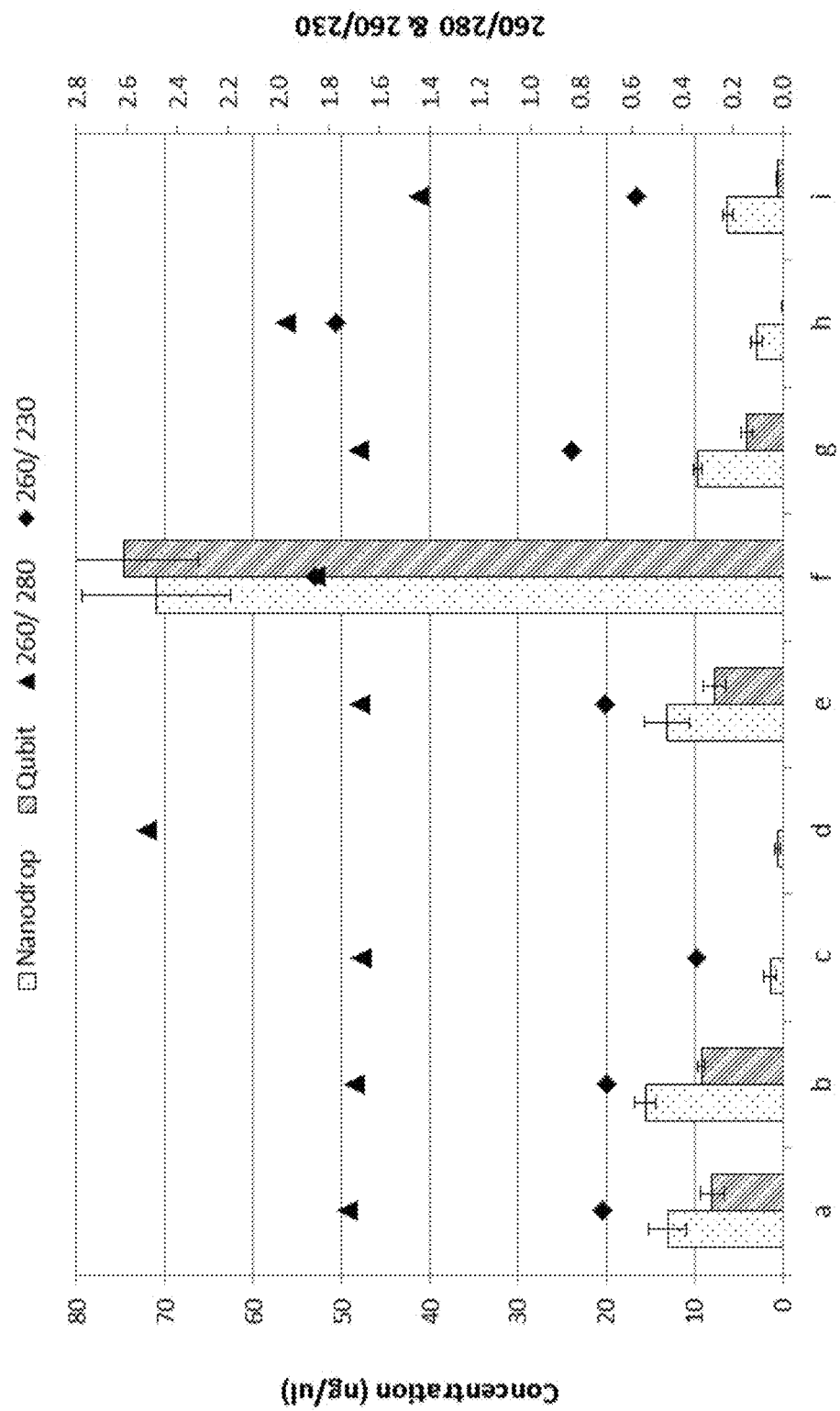

FIG. 1A provides analyses of DNA isolated from a human stool sample (Sample 1, Donor 1), the isolation carried out under interferent-removal conditions a)-i) described above. Results are presented as concentration of DNA using Nanodrop analysis ( ), Qubit analysis (\\\\), and as purity of DNA using a 260/280 ratio (▲) and a 260/230 ratio (♦).

Figure 1B:
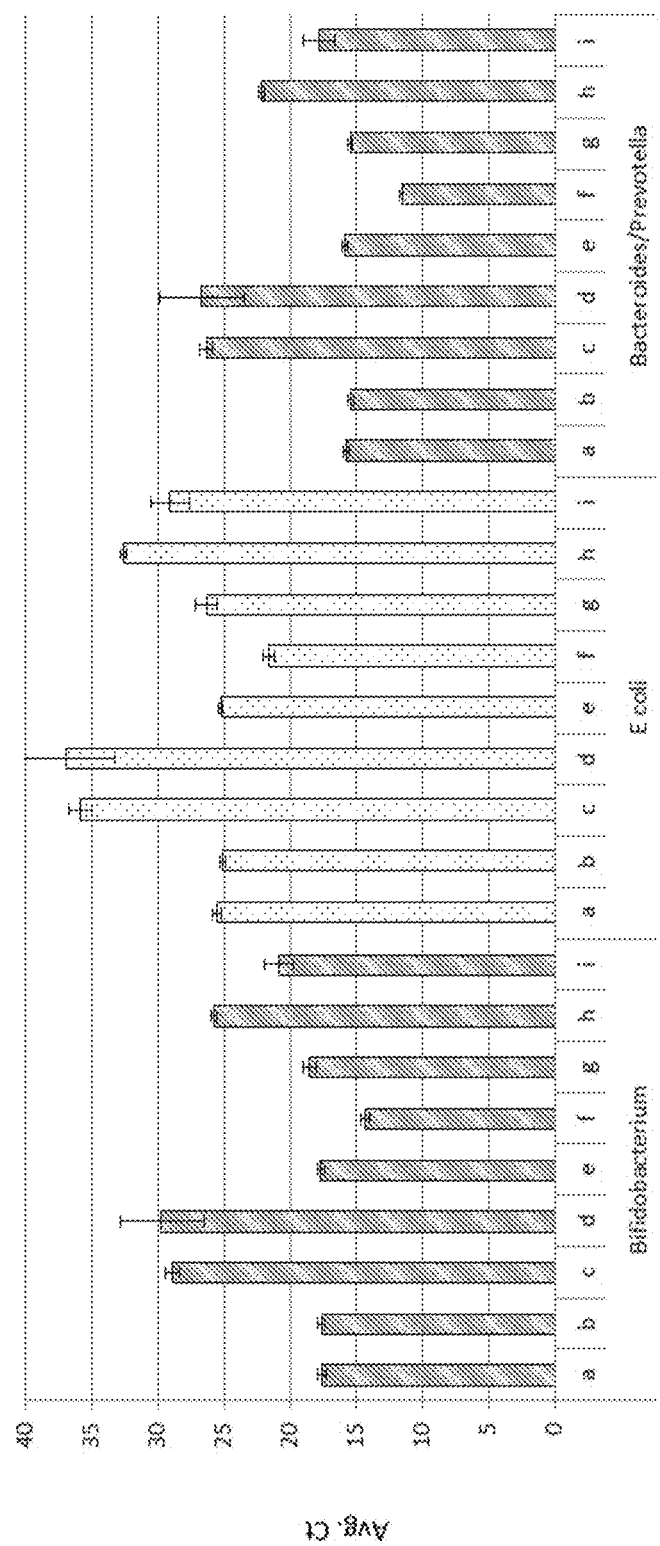

FIG. 1B provides a plot of average cycle threshold (Avg. $C_T$) levels of DNA isolated using Sample 1 and interferent-removal conditions a)-i) as described above for detection of each of three different bacterial targets: left set, gram positive *Bifidobacterium* (////); center set, gram negative *Escherichia coli* ( ); and right set, gram negative *Bacteroides/Prevotella* (////).

Figure 1C:
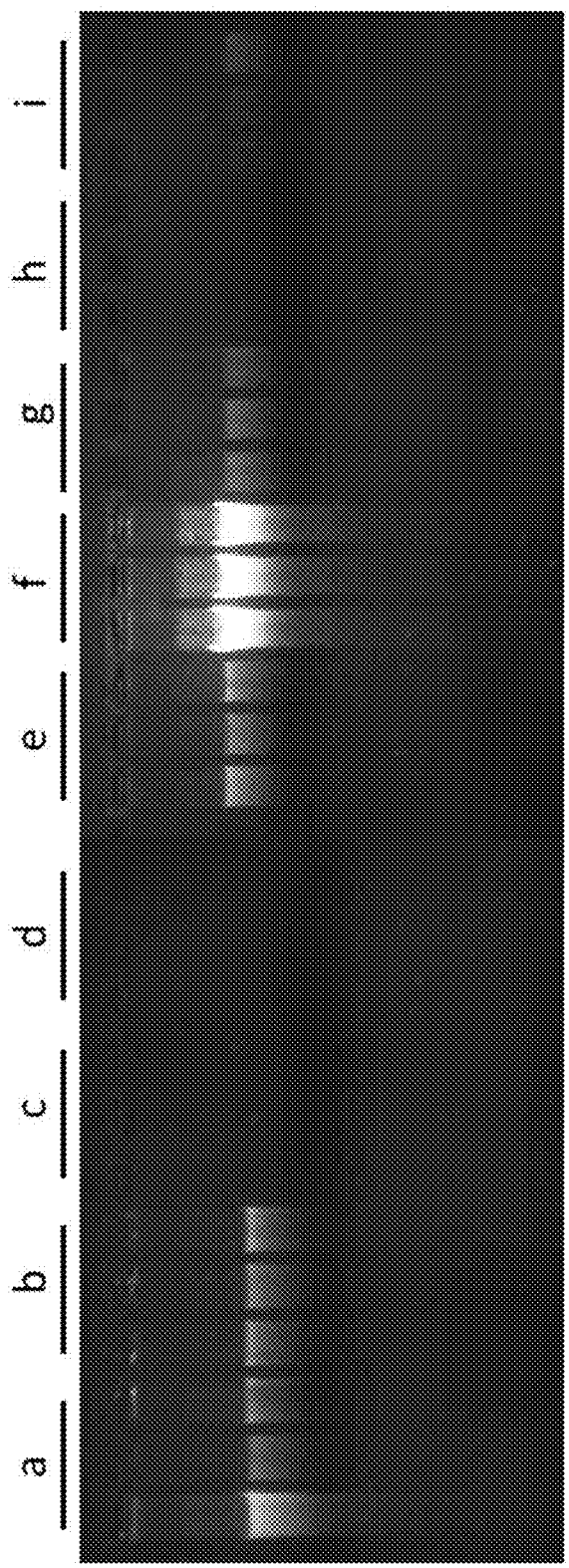

FIG. 1C provides results in triplicate from a 0.8% agarose gel electrophoretic analysis of DNA isolated from Sample 1 and for the conditions a)-i) as described above.

Figure 2A:
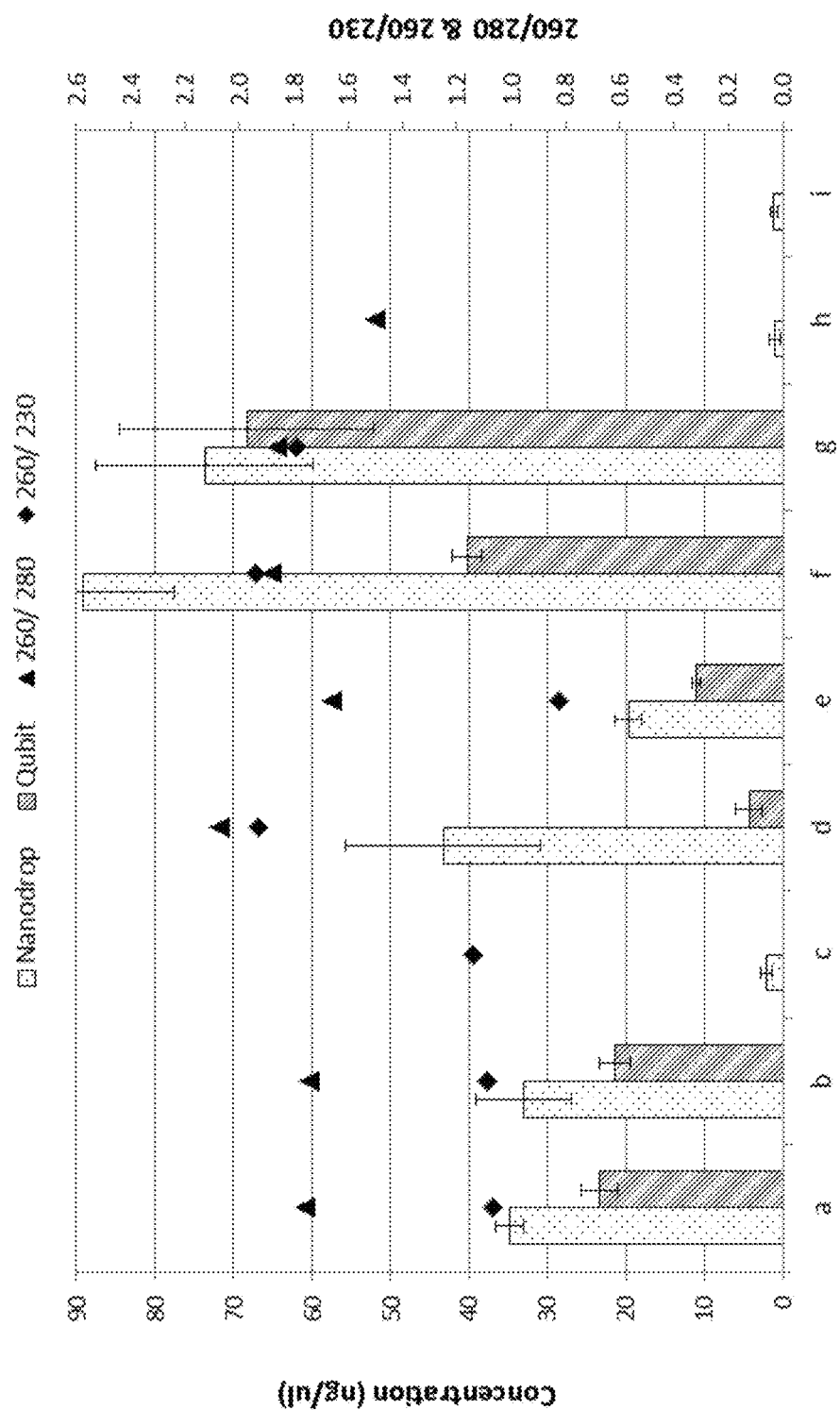

FIG. 2A provides analyses of DNA isolated from a stool sample of a second human (Sample 2, Donor 2), the isolation carried out under interferent-removal conditions a)-i) described above. Results are presented as concentration of DNA using Nanodrop analysis ( ), Qubit analysis (\\\\), and as purity of DNA using a 260/280 ratio (▲) and a 260/230 ratio (♦).

Figure 2B:
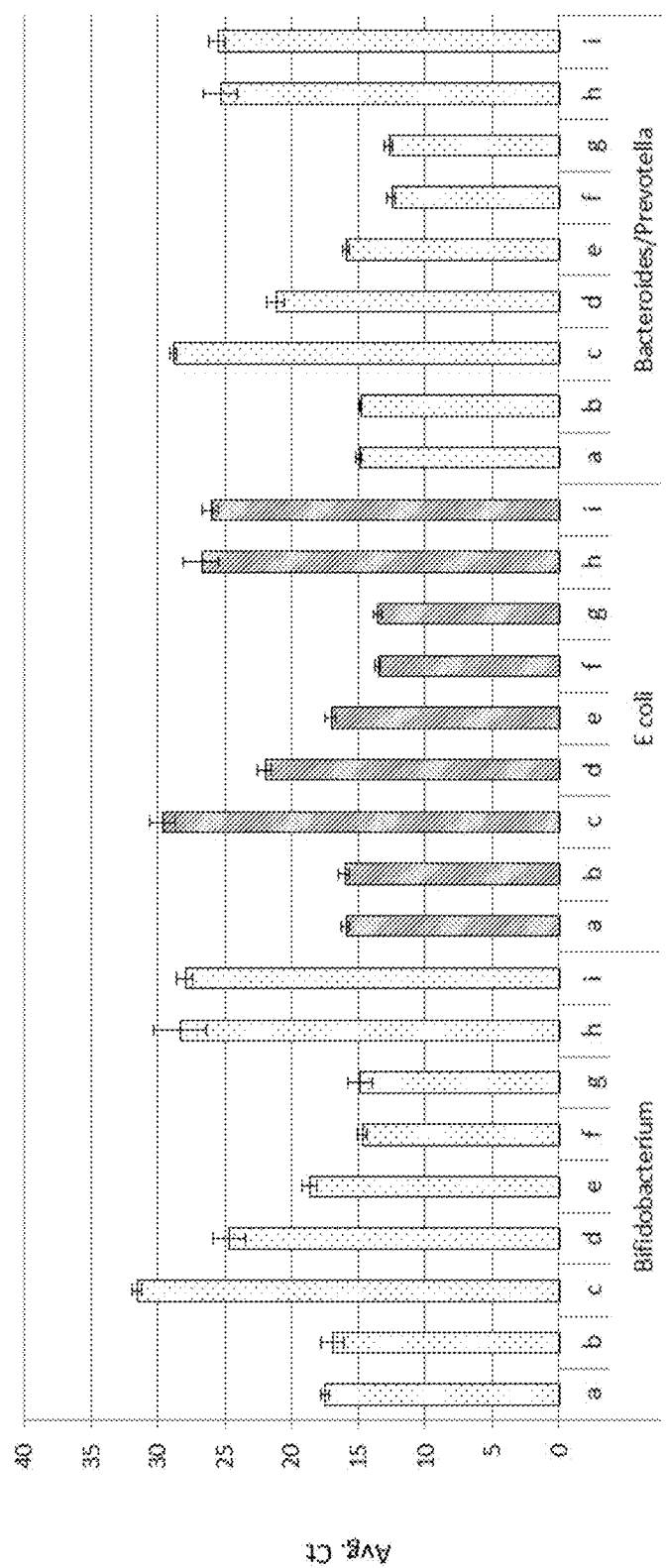

FIG. 2B provides a plot of average cycle threshold (Avg. $C_T$) levels of DNA isolated using Sample 2 and interferent-removal conditions a)-i) as described above for each of three different bacterial targets: left set, gram positive *Bifidobacterium* ( ) center set, gram negative *Escherichia coli* (\\\\); and right set, gram negative *Bacteroides/Prevotella* ( ).

Figure 2C:
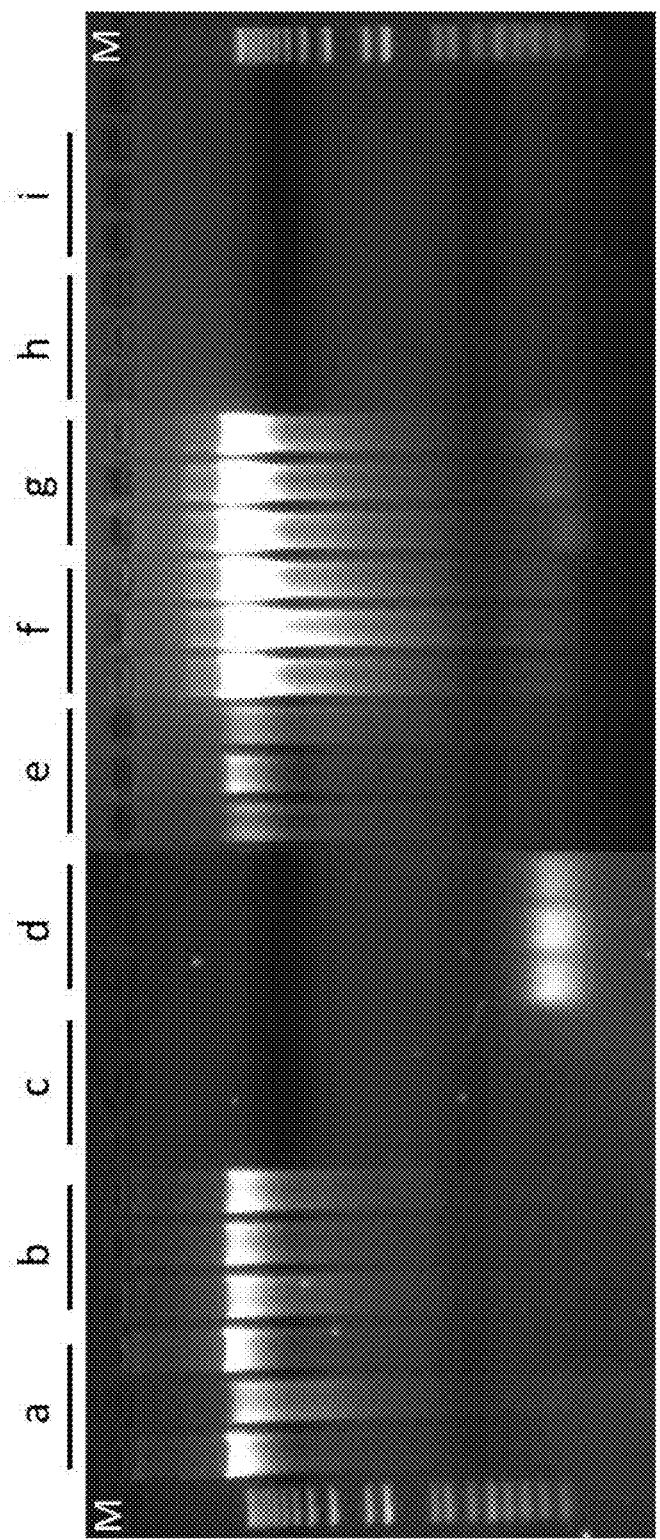

FIG. 2C provides results in triplicate from a 0.8% agarose gel electrophoretic analysis of DNA isolated from Sample 2 and interferent-removal conditions a)-i) cited above.

Figure 3A:
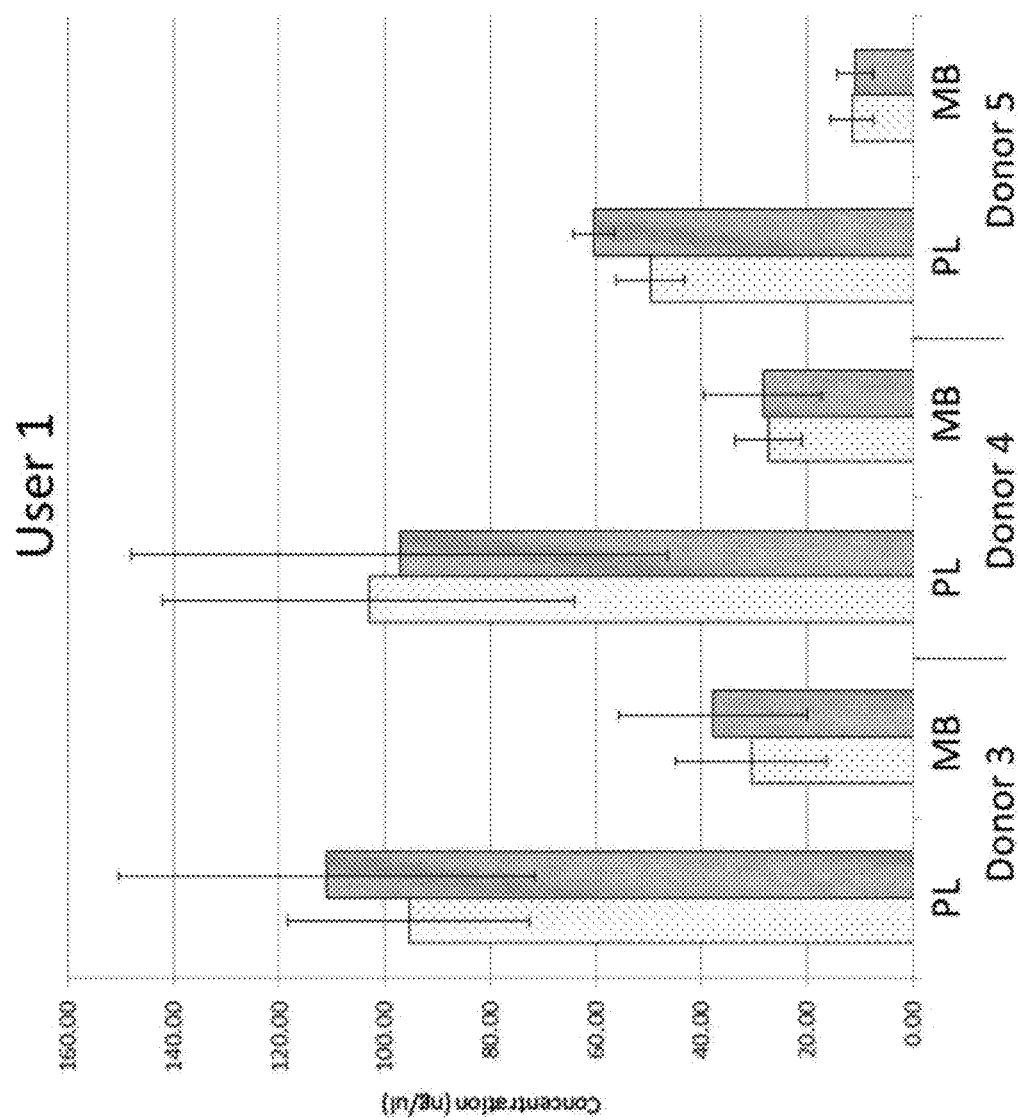

FIG. 3A provides User No. 1 analyses of DNA isolated from a stool sample of three different humans (Samples 3, 4, and 5 from Donors 3, 4, and 5, respectively). The concentration of DNA isolated using the interferent-removal methods substantially as described for condition f) above (designated PL in FIG. 3A-FIG. 3C) is compared with the concentration of DNA isolated using the PowerSoil® DNA Isolation Kit (MO BIO Laboratories, Inc.) as directed by the Kit instructions (designated MB in FIG. 3A-FIG. 3C) with the addition of a heat step prior to step one of the PowerSoil® Kit protocol to ensure an accurate comparison of the two methods. Results are presented as concentration of DNA (ng/µL) using Nanodrop analysis ( ) and Qubit analysis (////). Purity data are provided in the detailed description below.

Figure 3B:
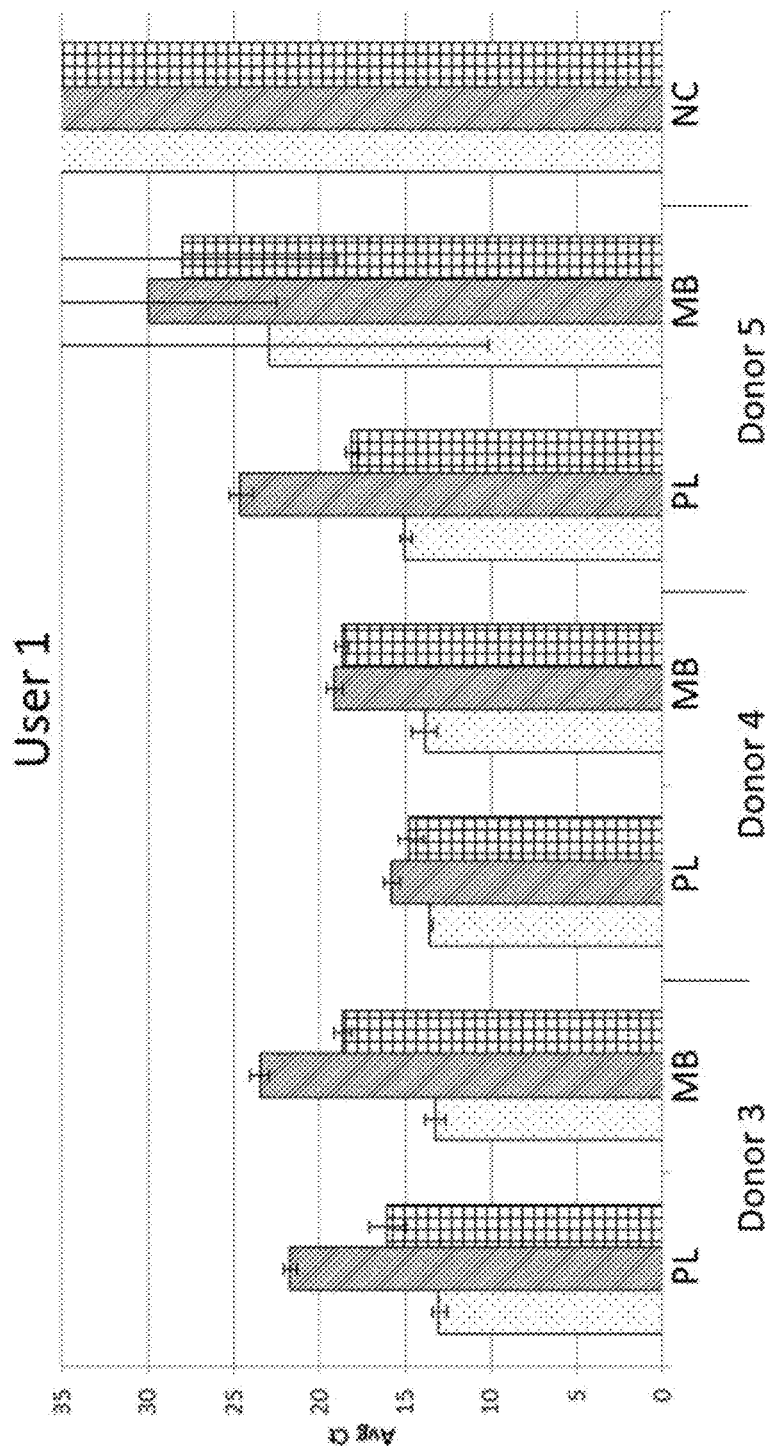

FIG. 3B provides a plot of average cycle threshold (Avg. $C_T$) levels of DNA isolated as for FIG. 3A by User No. 1 comparing the interferent removal process as described herein (PL) with the PowerSoil® DNA Isolation inhibitor removal process (MB) in the detection of each of three bacterial targets: gram positive *Bifidobacterium* (π), gram negative *Escherichia coli* (\\\\) and gram negative *Bacteroides/Prevotella* ( ). A heat step was included prior to step one of the PowerSoil® Kit protocol to ensure an accurate comparison with the interferent removal process used herein. NTC—non-treated control.

Figure 3C:
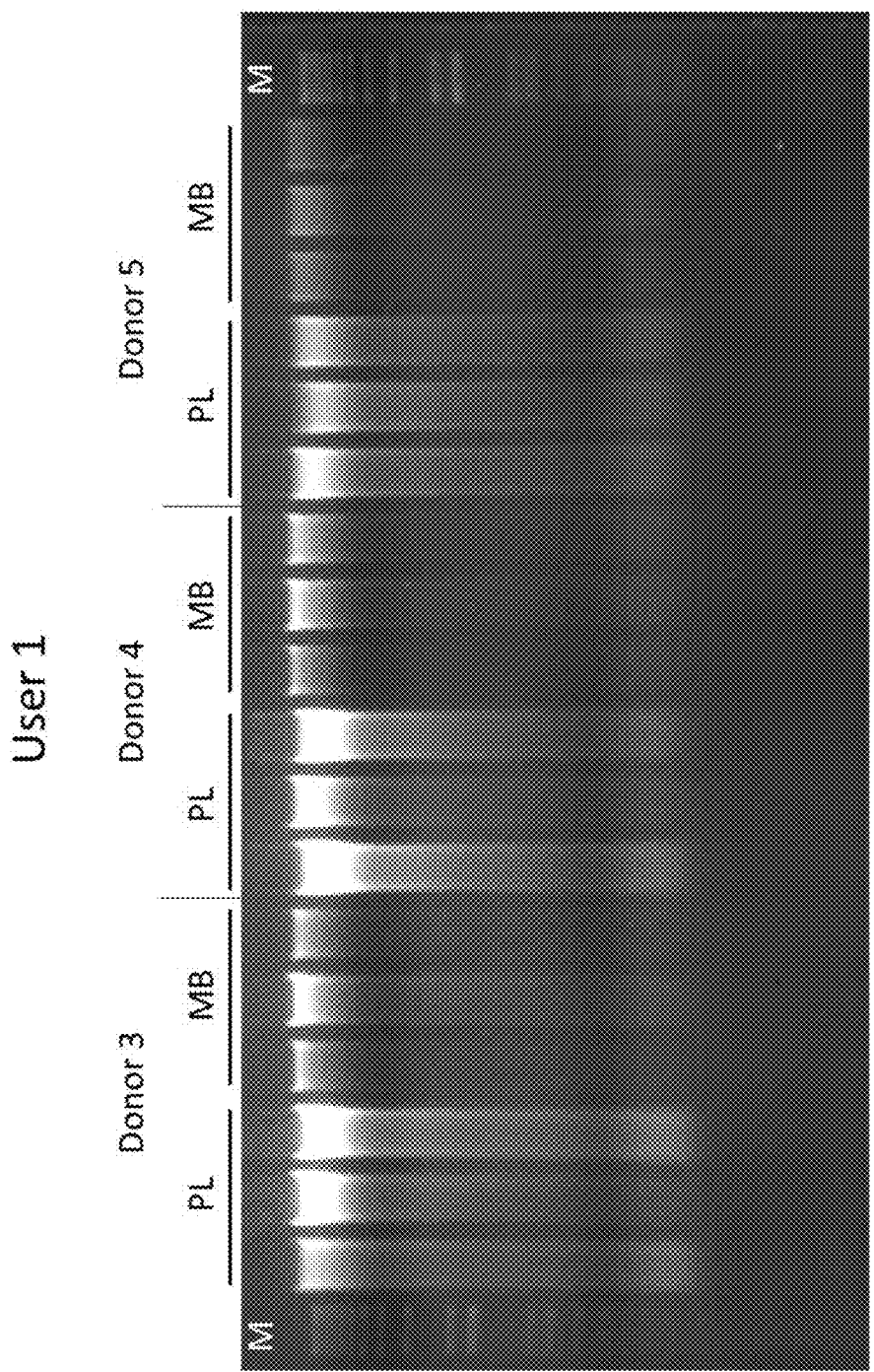

FIG. 3C provides results from a 0.8% agarose gel electrophoretic analysis of each of the triplicate isolations of each of Samples 3, 4 and 5. PL, results using the interferent-removal methods substantially as described for condition f); MB, results using the PowerSoil® DNA Isolation Kit as described for FIG. 3A.

Figure 4A:
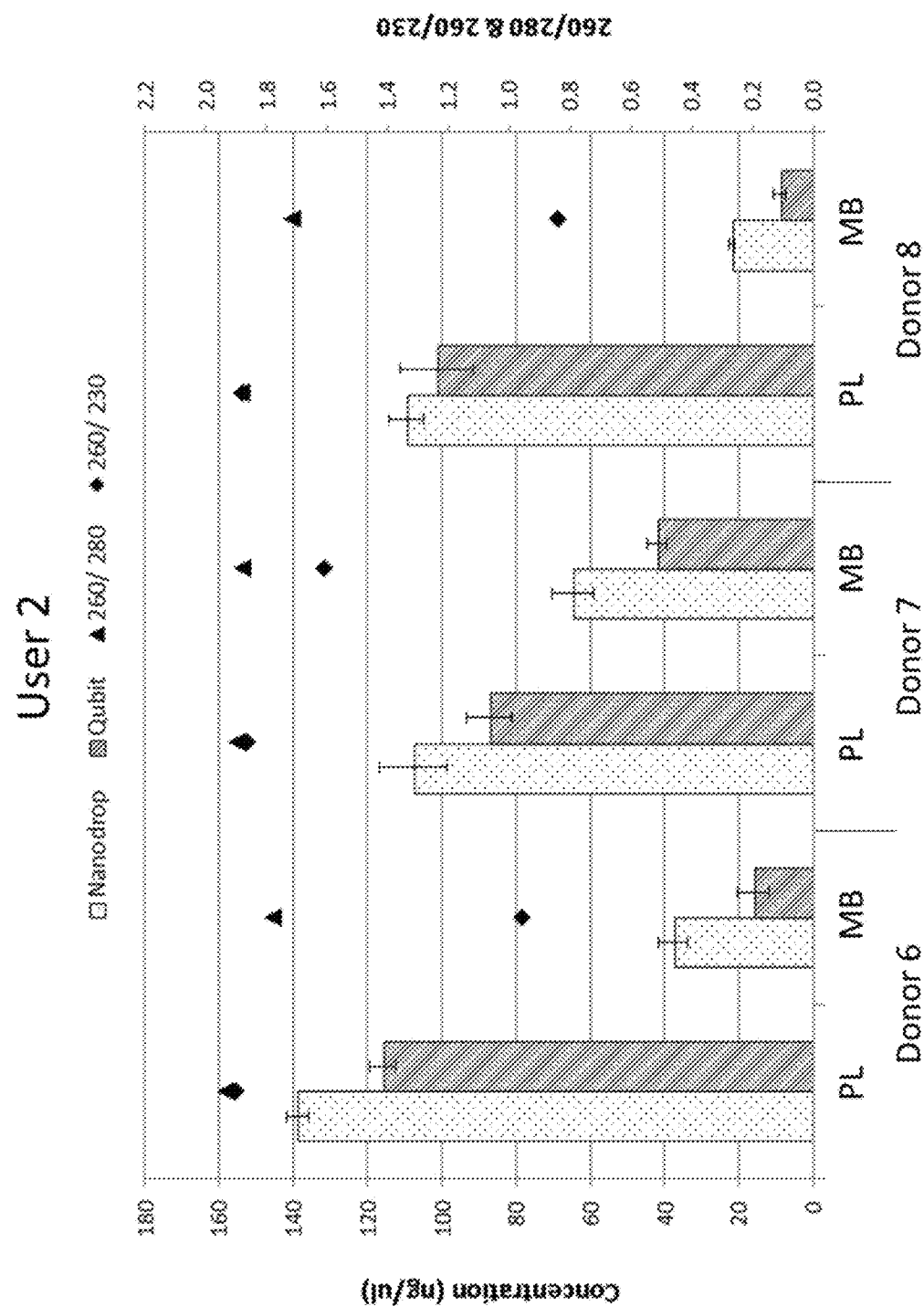

FIG. 4A provides User No. 2 analyses of DNA isolated from a stool sample of three different humans (Samples 6, 7, and 8 from Donors 6, 7, and 8, respectively). The concentration of DNA isolated using the interferent-removal methods substantially as described for condition f) above (designated PL in FIG. 4A-FIG. 4C) is compared with the concentration of DNA isolated using the PowerSoil® DNA Isolation Kit (MO BIO Laboratories, Inc.) as directed by the Kit instructions (designated MB in FIG. 4A-FIG. 4C) with the addition of a heat step prior to step one of the PowerSoil® Kit Protocol to ensure an accurate comparison of the two methods. Results are presented as concentration of DNA (ng/µL) using Nanodrop analysis ( ), Qubit analysis (\\\\), and as purity of DNA using a 260/280 ratio (▲) and a 260/230 ratio (♦).

Figure 4B:
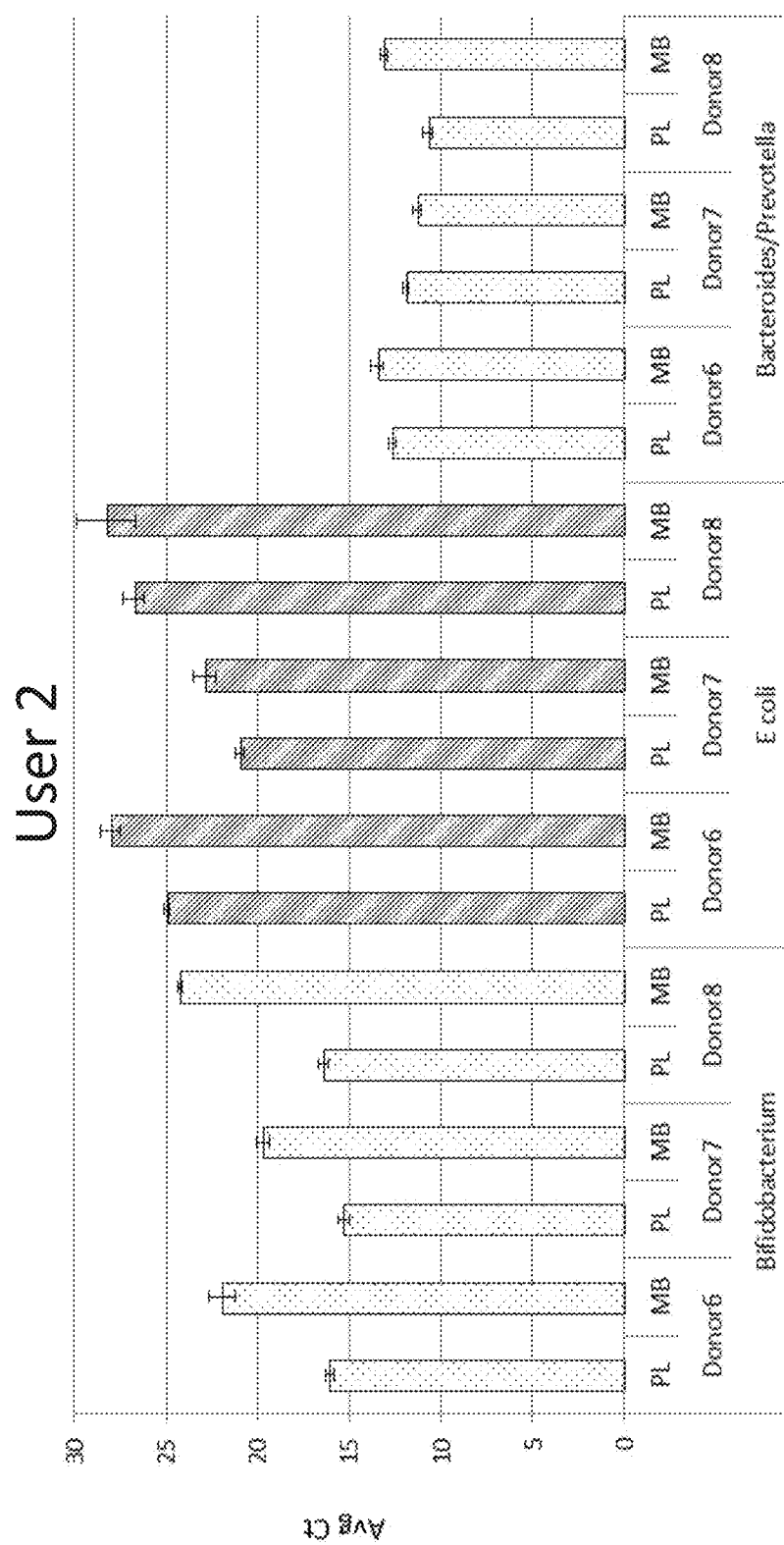

FIG. 4B provides a plot of average cycle threshold (Avg. $C_T$) levels of DNA isolated as for FIG. 4A by User No. 2 comparing the interferent removal process as described herein (PL) with the PowerSoil® DNA Isolation inhibitor removal process (MB) in the detection of each of the bacterial targets: gram positive *Bifidobacterium* ( ), gram negative *Escherichia* (\\\\) and gram negative *Bacteroides/Prevotella* ( ). A heat step was included prior to step one of the PowerSoil® Kit protocol to ensure an accurate comparison with the interferent removal process used herein.

Figure 4C:
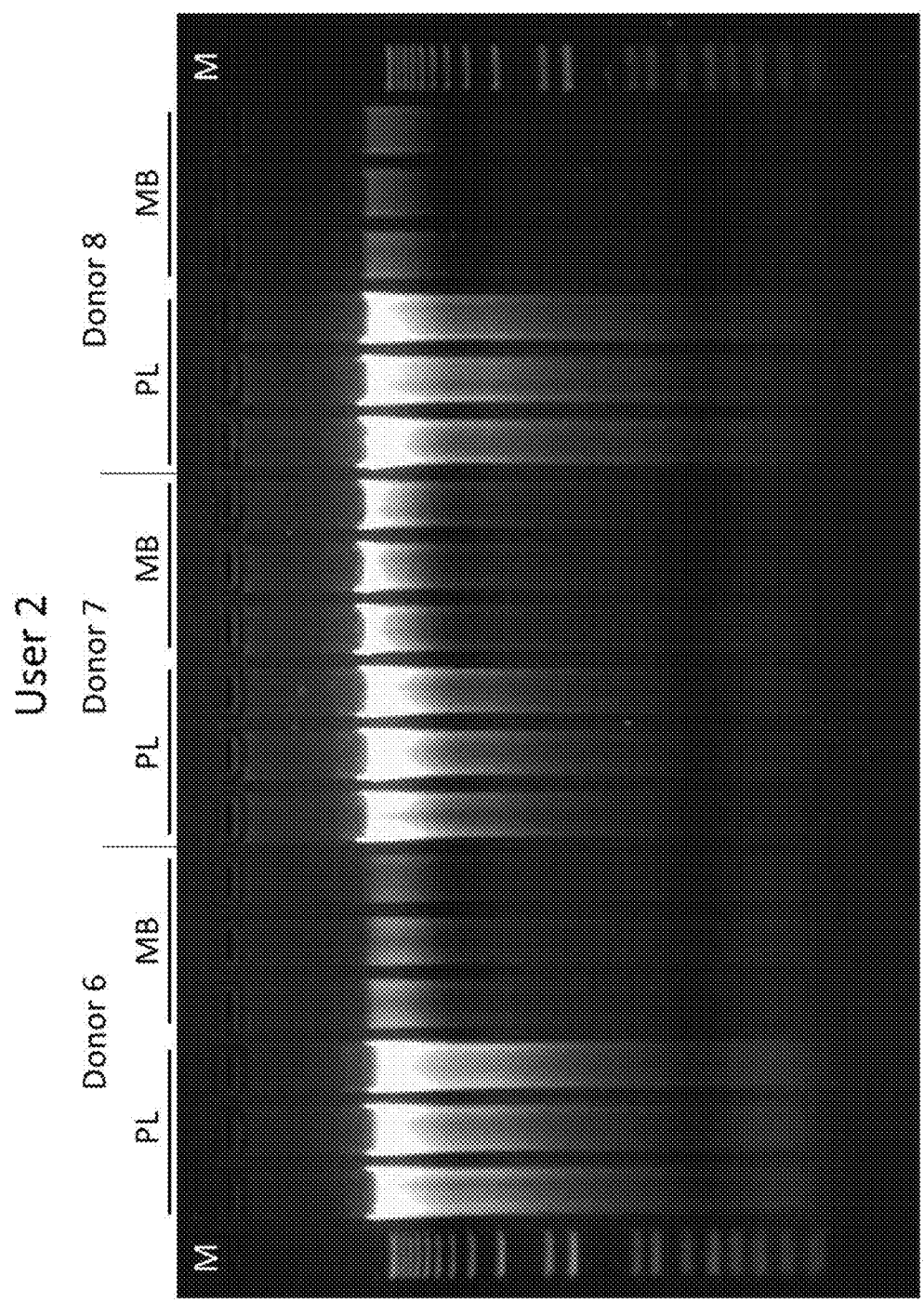

FIG. 4C provides results from a 0.8% agarose gel electrophoretic analysis of each of the triplicate isolations of each of Samples 6, 7, and 8. PL, results using the interferent-removal methods substantially as described for condition f); MB, results using the PowerSoil® DNA Isolation Kit as described for FIG. 3A.

Figure 5A:
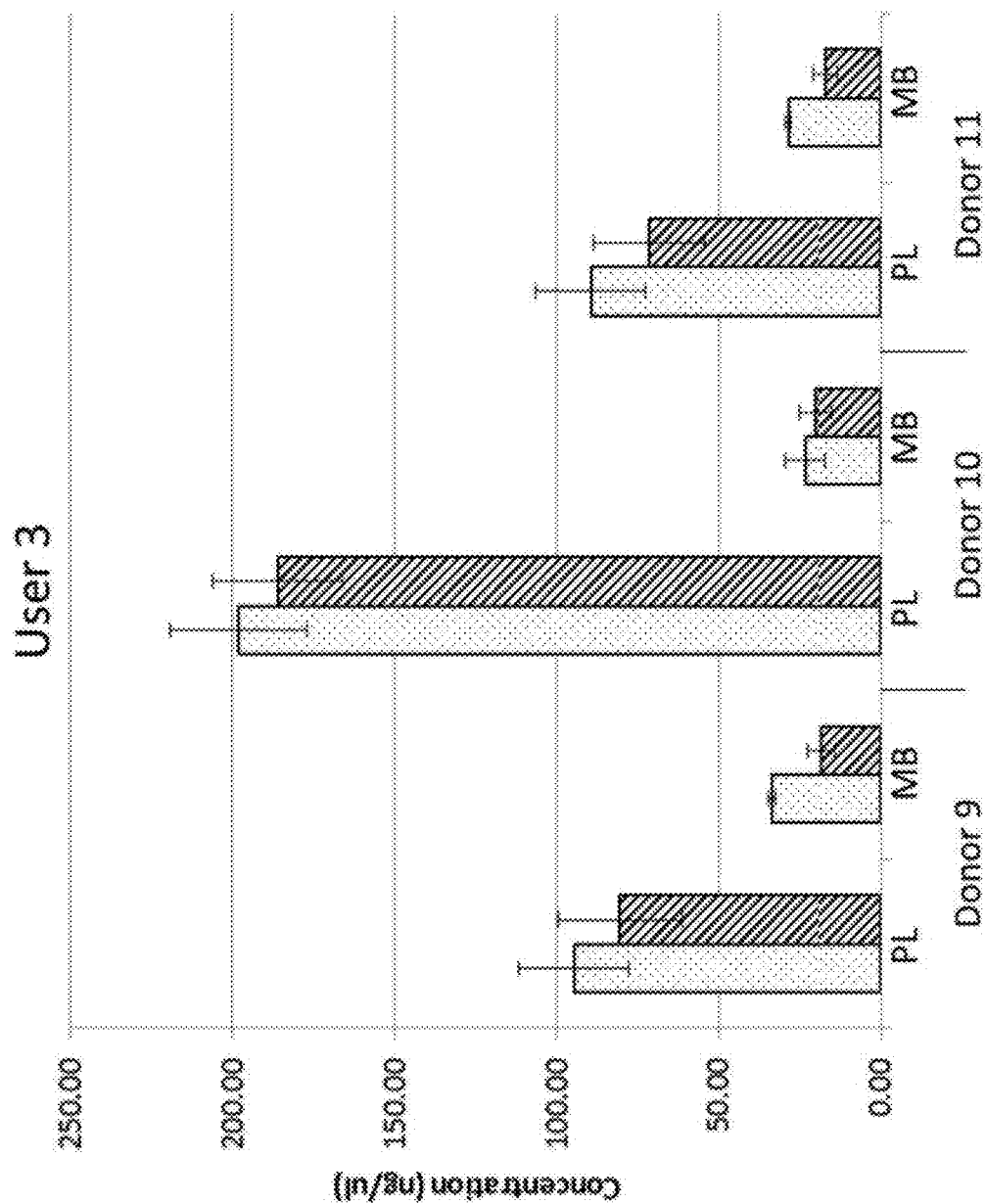

FIG. 5A provides User No. 3 analyses of DNA isolated from a stool sample of three different humans (Samples 9, 10, and 11 from Donors 9, 10, and 11, respectively). The concentration of DNA isolated using the interferent-removal methods substantially as described for condition f) above (designated PL in FIG. 5A-FIG. 5C) is compared with the concentration of DNA isolated using the PowerSoil® DNA Isolation Kit (MO BIO Laboratories, Inc.) as directed by the Kit instructions (designated MB in FIG. 5A-FIG. 5C) with the addition of a heat step prior to step one of the PowerSoil® Kit protocol to ensure an accurate comparison of the two methods. Results are presented as concentration of DNA (ng/µL) using Nanodrop analysis ( ) and Qubit analysis (\\\\).

Figure 5B:
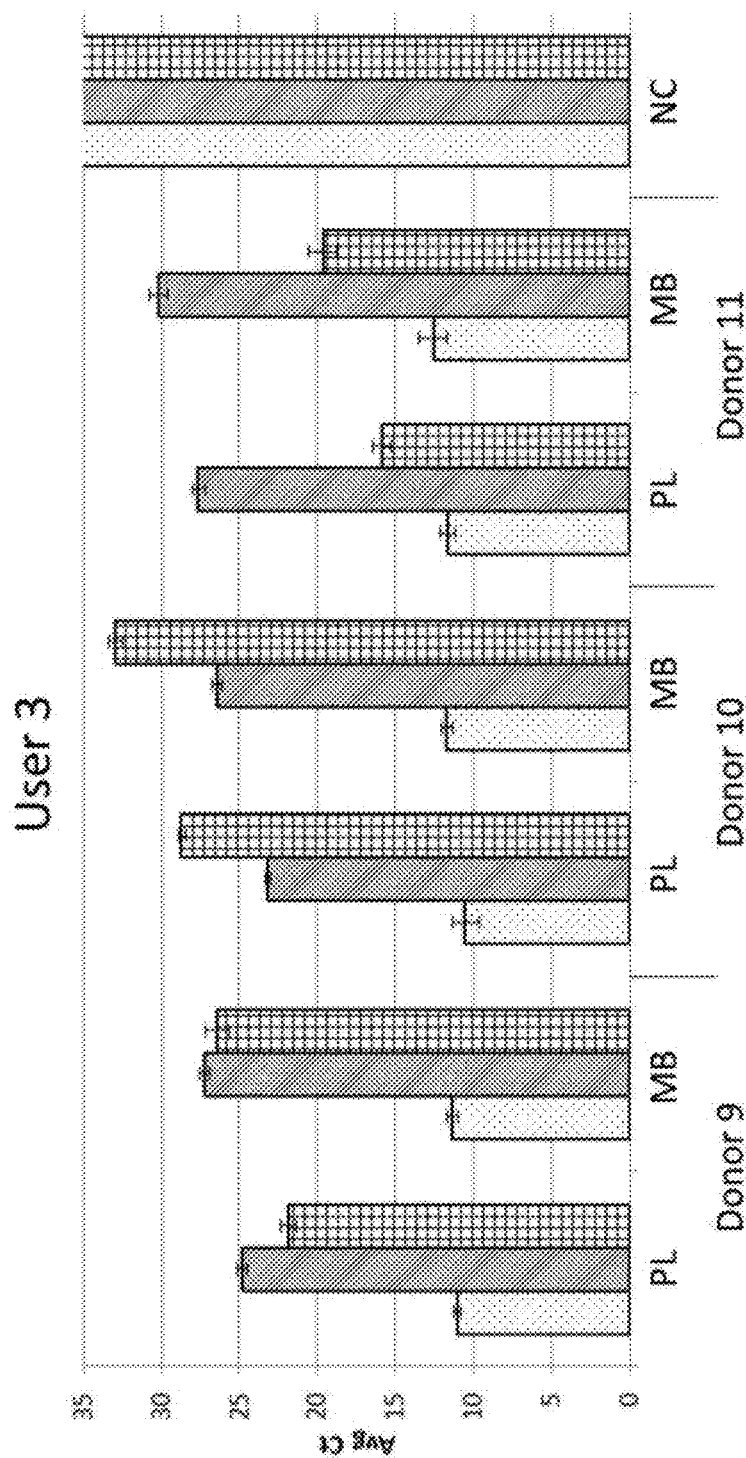

FIG. 5B provides a plot of average cycle threshold (Avg. $C_T$) levels of DNA isolated as for FIG. 5A by User No. 3 comparing the interferent removal process as described herein (PL) with the PowerSoil® DNA Isolation inhibitor removal process (MB) in the detection of each of three bacterial targets: gram positive *Bifidobacterium* (#), gram negative *Escherichia coli* (\\\\) and gram negative *Bacteroides/Prevotella* ( ). A heat step was included prior to step one of the PowerSoil® Kit protocol to ensure an accurate comparison with the interferent removal process used herein. NTC—non-treated control.

Figure 5C:
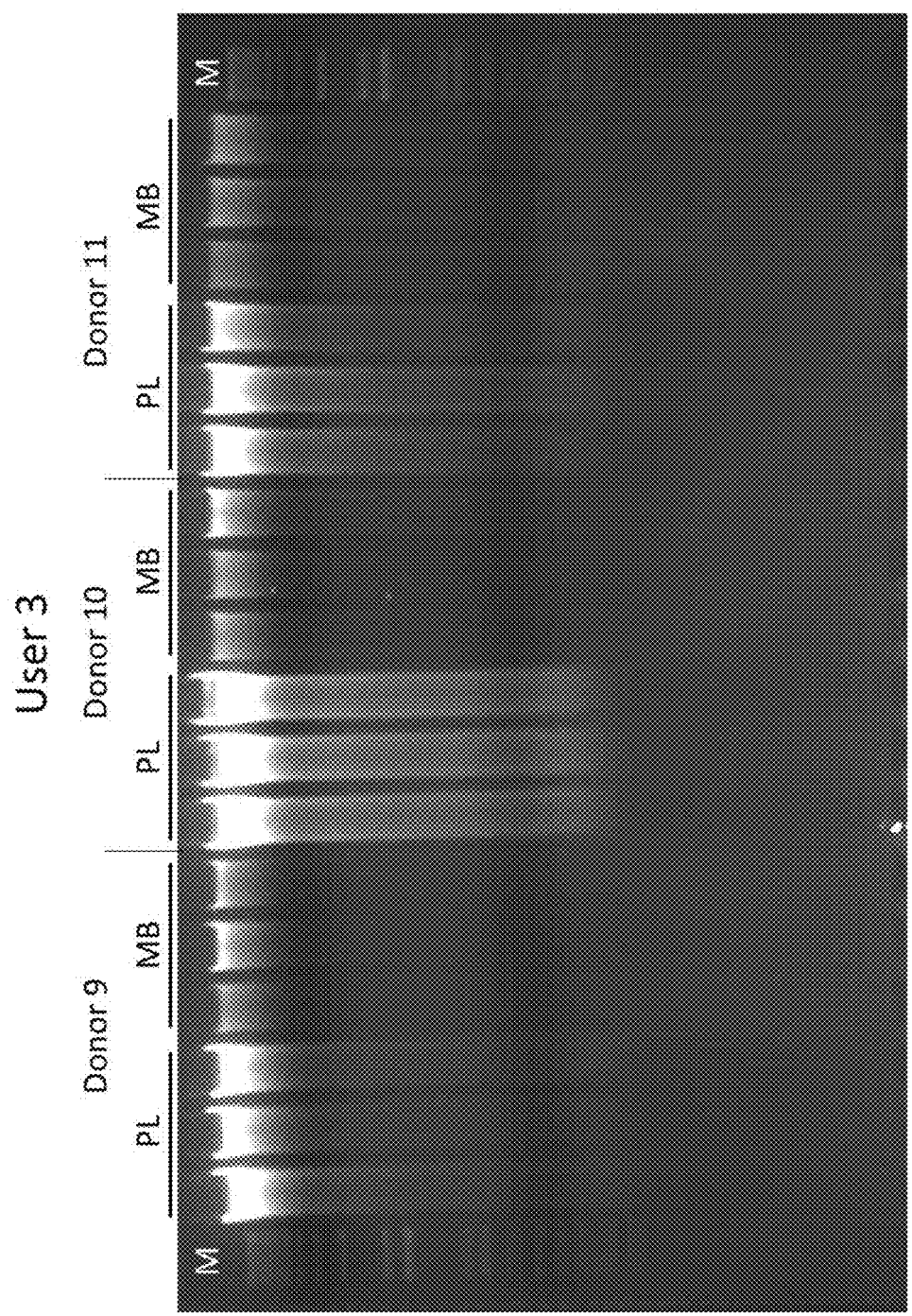

FIG. 5C provides results from a 0.8% agarose gel electrophoretic analysis of each of the triplicate isolations of each of Samples 9, 10 and 11. PL, results using the interferent-removal methods substantially as described for condition f); MB, results using the PowerSoil® DNA Isolation Kit as described for FIG. 5A.

FIG. 6 provides identification of various genera of bacteria present using sequencing analysis of DNA isolated from human stool by 16S rRNA gene sequencing. Samples from Donor 12 (D12) and Donor 13 (D13) were processed in triplicate to generate isolated DNA as presented herein. Sequencing and bioinformatics were carried out by Diversigen (formerly Metanome Inc., Two Greenway Plaza, suite 910, Houston, Tex.). Representation of top bacterial genera is shown as a percentage of total reads.

Figure 7:
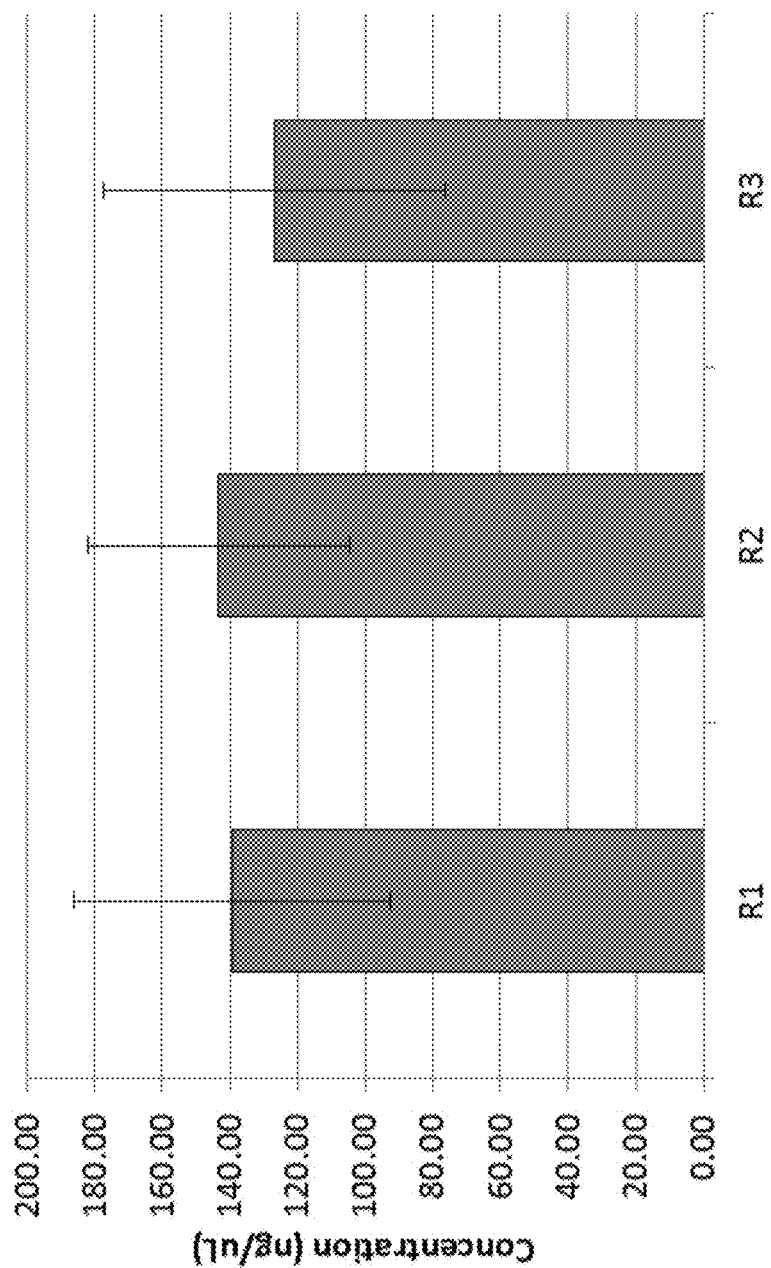

FIG. 7 provides plots of DNA yield in ng/µL from samples of rat stool (one pellet, 0.1-0.15 g) from three donors, each carried out in triplicate.

Figure 8:
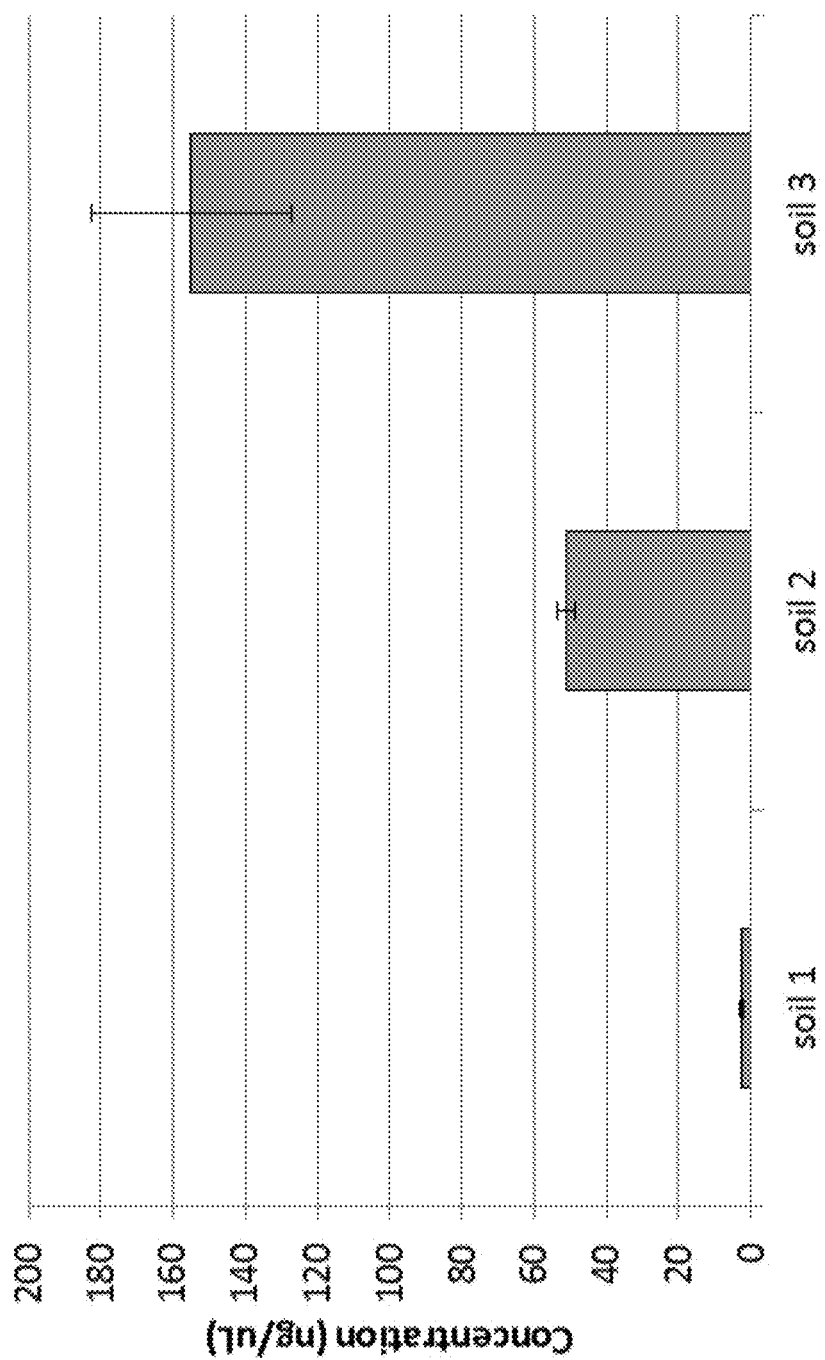

FIG. 8 provides plots of DNA yield in ng/µL from three samples of soil (0.2±0.05 g), each carried out in triplicate.

DESCRIPTION OF VARIOUS EMBODIMENTS

It is to be understood that both the foregoing general description and the following detailed description are exemplary and explanatory only and are not intended to limit the scope of the current teachings. In this application, the use of the singular includes the plural unless specifically stated otherwise. The use of "comprise", "contain", and "include", or modifications of those root words, for example but not limited to, "comprises", "contained", and "including", are not intended to be limiting. Use of "or" means "and/or" unless stated otherwise. The term "and/or" means that the terms before and after can be taken together or separately. For illustration purposes, but not as a limitation, "X and/or Y" can mean "X" or "Y" or "X and Y." As used herein and unless otherwise indicated, the terms "a" and "an" are taken to mean "one," "at least one" or "one or more."

Whenever a range of values is provided herein, the range is meant to include the starting value and the ending value and a value or value range there between unless otherwise specifically stated. For example, "from 0.2 to 0.5" means 0.2, 0.3, 0.4, 0.5; ranges there between such as 0.2-0.3, 0.3-0.4, 0.2-0.4; increments there between such as 0.25, 0.35, 0.225, 0.335, 0.49; increment ranges there between such as 0.26-0.39; and the like.

The section headings used herein are for organizational purposes only and are not to be construed as limiting the subject matter described in any way. All literature and similar materials cited in this application including, but not limited to, patents, patent applications, articles, books, treatises, and internet web pages, regardless of the format of such literature and similar materials, are expressly incorporated by reference in their entirety for any purpose. In the event that one or more of the incorporated literature and similar materials defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Sample Collection and Storage: Collected samples may be dried, shipped, refrigerated, frozen at −20° C. or −80° C., or used immediately for analysis. For embodiments wherein RNA is analyzed or isolated, a stabilization agent may be present in, or added to, the collection vessel, e.g., the RNAlater™ Stabilization Solution (Thermo Fisher Scientific, Cat No. AM7021).

Lysis: A major challenge in working with environmental or biological samples is not the ability to extract nucleic acid per se, but isolation of nucleic acid that accurately represents the nucleic acid in the sample. This is true particularly for microbiome-containing samples that contain a diverse microbial population due to the substantial difference in the compositions of different microbial cell walls which is a major impediment to effective lysis of all cells. For example, Gram-negative bacteria can often be efficiently lysed with heat alone, while Gram-positive bacteria, with their thicker and more complex cell walls (most conspicuously, the addition of teichoic acid into the peptidoglycan layer), often require an additional mechanical, enzymatic or chemical lysis.

Lysis of microorganisms present in environmental or biological samples such as soil and stool can be carried out using heat, chemical lysis, enzymatic lysis, mechanical disruption or any combination of these methods as known in the art. Chemical lysis includes the use of denaturants such as an alcohol, chaotropic agents such as guanidinium chloride, guanidine thiocyanate, urea, or lithium salts, and/or detergents including nonionic, cationic, anionic (sodium dodecyl sulfate) or zwitterionic detergents, or use of acid or alkaline lysis. Mechanical disruption includes the use of bead beating and/or homogenizing methods. Enzymatic lysis includes the use of a protease, amylase, cellulose, or a lipase, for example, followed by optional inactivation of the enzyme.

A collected sample is thoroughly mixed to generate a homogeneous sample before weighing a portion for the methods herein. For use in a 2 mL bead tube, 0.2 g±0.05 g of a large animal stool sample or of an environmental sample is used. For a small animal stool sample, an amount of 0.1±0.05 g was used. These sample amounts can be adjusted accordingly depending on the volume of the tube used in the methods herein.

For the studies herein, 100 micron Acid Washed Zirconium Beads (OPS Diagnostics, Lebanon, N.J.) were used in bead beating for disrupting an environmental or biological sample at 1200 mg per Sarstedt 2 mL tube. Bead beating for 10 min on a vortex mixer with a horizontal adapter (Ambion™ Vortex Adapter, Catalog No. AM10024, Thermo Fisher Scientific, Waltham, Mass.) or 2-5 min on a high power bead beater (such as the Omni Bead Ruptor Homogenizer, OMNI Intl, Kennesaw, Ga.) provided effective processing of samples as measured by DNA yield, qPCR and agarose gel analysis. Disruption may use other bead beating tubes from kits known in the art such as the bead beating tubes from the PREPSEQ™ Rapid Spin Sample Prep Kit (Thermo Fisher Scientific, Cat No. 4468304).

A combination of chemical lysis, heating and mechanical disruption is used herein although any lysis method is satisfactory that maximally achieves lysis of microbes within an environmental or biological sample while protecting nucleic acid quality and yield. Lysis may occur in a buffer of physiological pH, a pH of 6.0 to 8.0, from pH 6.5 to 7.5, or at pH 7.0. Enhanced lysis was obtained by using a chemical treatment with a chaotropic agent during sample dispersion followed by optional addition of a detergent prior to a heat treatment. Heating prior to bead-beating at 65° C. for 10 minutes or 95° C. for 5 minutes resulted in greater yield of nucleic acid. Lysis in the presence of phosphate buffer enhanced later binding of DNA to a solid support, resulting in increased yield and quality of DNA.

Optionally, a nonionic, cationic, anionic or zwitterionic detergent may be present during the disrupting step. Nonionic detergents include TRITON™ X-100 (octylphenol ethoxylate having an average of 9.5 ethoxylate groups (Dow Chemical Company Product Information, Form No. 119-01882, JMS1206), TRITON™ X-114 (octylphenol ethoxylate having an average of 7.5 ethoxylate groups (Dow Chemical Company Product Information, Form No. 119-01884, JMS1206), NONIDET™ P-40 (octylphenolpoly(ethyleneglycolether) (Roche Diagnostics GmbH, Catalog No. 11 332 473 001, July 2005), THESIT™ (dodecyl alcohol polyoxyethylene ether IUPAC Name 2-dodecoxyethanol) CAS Number 9002-92-0; Chemical Formula $C_{14}H_{30}O_2$), BRIJ™-35 (polyoxyethyleneglycol dodecyl ether), BRIJ™-58(polyoxyethylene 20 cetyl ether), TWEEN™ 20 (polyoxyethylene sorbitan monolaurate), TWEEN™ 80 (polyoxyethylene sorbitan monooleate), octyl glucoside, and octyl thioglucoside, for example. Cationic detergents include quaternary ammonium salts such as CTAB (cetyltrimethylammonium bromide), for example. Anionic detergents include sodium dodecyl sulfate (SDS), sodium lauryl sulfate, lithium dodecyl sulfate, deoxycholic acid, and sarkosyl, for example. Zwitterionic detergents include CHAPS (3-[(3-cholamidopropyl)dimethylammonio]-1-propanesulfonate), and CHAPSO (3-[(3-cholamidopropyl)dimethylammonio]-2-hydroxy-1-propanesulfonate), for example.

Interferent Depletion: A single precipitation step depletes substances that interfere with subsequent analysis of isolated nucleic acid. For example, the methods provide for reducing, depleting, or removing an inhibitor of a DNA dependent enzyme from the lysate, volume portion of lysate thereof, supernatant thereof, or volume portion of supernatant thereof, such that the resulting concentration of inhibitor is below a threshold level that can inhibit that enzyme reaction. As such, a given volume of lysate or lysate supernatant of an environmental or biological sample has a greater amount of the enzyme inhibitor than the equivalent volume of an inhibitor-depleted solution of that sample. Similarly, a given volume of lysate or lysate supernatant of an environmental or biological sample has a greater amount of a hybridization inhibitor than the equivalent volume of an inhibitor-depleted solution of that sample.

After lysis, the lysate, a volume portion of the lysate, a supernatant obtained from the lysate, or a volume portion of a lysate supernatant (for example, up to 400 μL of a lysate supernatant) is contacted with an interferent removal composition. The interferent removal composition comprises ammonium acetate and a flocculant and can be made up in a stock solution at any concentration that remains in solution. Final exemplary concentrations for each of the ammonium acetate and the flocculant (after mixing the stock solution with lysate, a volume portion thereof, a supernatant thereof, or a volume portion of supernatant thereof) is from 5 mM to 200 mM each, from 10 mM to 175 mM each, from 20 mM to 160 mM each, from 30 mM to 150 mM each, from 40 mM to 140 mM each, from 50 mM to 130 mM each, from 5 mM to 50 mM each, from 10 mM to 50 mM each, from 15 mM to 50 mM each, from 20 mM to 50 mM each, or from 25 mM to 50 mM each. In an embodiment, the concentration of each of the ammonium acetate and the flocculant is substantially equimolar.

In one embodiment, the final concentration of ammonium acetate and flocculant (upon mixing with the lysate, volume portion thereof, lysate supernatant or volume portion thereof) is 15 mM to 70 mM ammonium acetate and 15 mM to 70 mM flocculant. In one embodiment, the concentration of ammonium acetate and flocculant is substantially equimolar, i.e., at equimolar concentrations ±30%. In an embodiment, the ammonium acetate and flocculant are added as solid ingredients to yield the final concentrations in the interferent removal step cited above.

The flocculant comprises aluminum ammonium sulfate, ammonium sulfate dodecahydrate, aluminum ammonium sulfate dodecahydrate, aluminum potassium sulfate, aluminum chlorohydrate, aluminum sulfate, calcium oxide, iron (III) chloride, iron (II) sulfate, sodium aluminate, sodium silicate, or a combination thereof. In an embodiment, the flocculant is aluminum ammonium sulfate, ammonium sulfate dodecahydrate, aluminum ammonium sulfate dodecahydrate, aluminum potassium sulfate, aluminum chlorohydrate, aluminum sulfate, calcium oxide, iron (III) chloride, iron (II) sulfate, sodium aluminate, sodium silicate, or a combination thereof. In an embodiment, the flocculant is aluminum ammonium sulfate dodecahydrate.

An interferent precipitated by addition of the composition comprises, for example, humic substances including humic acid, humic polymers and humin; polyphenols, polysaccharides, plant pigments, plant cell walls, chitins, fulvic acid, tannins, phenolic compounds, bile, bilirubin, or undigested or partially digested fiber, or undigested or partially digested food, for example. The supernatant resulting from removal of an interferent is referred to herein as a nucleic acid-containing, interferent-depleted solution, i.e., a solution that has been depleted of materials that would inhibit later nucleic acid analyses. In an embodiment, the interferent-depleted solution is a supernatant.

Precipitation of interferents is at a temperature that maximally removes interferents without compromising yield or quality of isolated nucleic acid. Laboratory temperatures ranging from that of an ice bath to ambient temperature can be used. Once the interferent depletion composition is added to the lysate, volume portion thereof, supernatant thereof, or volume portion thereof, an interferent-containing precipitate may form immediately and the nucleic acid-containing, interferent-depleted solution may be obtained immediately, although the contacting step may be from a few seconds to a few minutes or up to 5 or 10 minutes or up to an hour or as much as an hour. If refrigerated, longer lengths of time may be used such as overnight, for example.

Isolation of Nucleic Acid: Isolation of DNA present in the interferent-depleted solution is accomplished by known methods, including that of binding DNA to a solid support, followed by a washing step and elution of bound DNA. Binding to a solid support and washing in the presence of a chaotrope such as guanidine hydrochloride can be carried out as for the PURELINK™ Genomic DNA Kit (Invitrogen Cat. No. K1820, Thermo Fisher Scientific, Inc.) following kit protocols after the lysate generation step. While an alcohol such as ethanol or isopropanol at a concentration of up to 10% or 20% may be present during binding, use thereof is optional for binding DNA in the present methods. A washing step may be repeated and a washing buffer may include Tris buffer, NaCl, and alcohol such as ethanol or isopropanol.

Isolation of RNA present in the interferent-depleted solution is accomplished by known methods, including that of binding RNA to a solid support, followed by a washing step and elution of bound RNA. The MAGMAX™ MIRVANA™ Total RNA Isolation Kit (Applied Biosystems Cat No. A27828, Thermo Fisher Scientific, Inc.) is an example of a kit that uses magnetic-bead technology and that enables recovery of RNA, including small RNA such as microRNA from a sample. Further kits include the PURELINK™ Pro 96 total RNA Purification Kit (Thermo Fisher Scientific, Inc. Cat. No. 12173-011A) and the RIBOPURE™ RNA Purification Kit (Thermo Fisher Scientific Inc. Cat No. AM1925). Isolation of RNA is best carried out immediately after removal of interferents so as to maintain high quality RNA following kit protocols after the lysate generation step.

A solid support may be a mineral support or a polymer support. A mineral or polymer support includes supports involving silica and the silica may be glass. Supports include, but are not limited to, beads, columns and filters. In an embodiment, the mineral or polymer support is a glass fiber filter, spin filter, column, spin column, or a magnetic bead. The solid support having nucleic acids bound thereto may be centrifuged, filtered, or dialyzed, for example, for washing the bound nucleic acid or for elution of bound nucleic acid.

Standard elution buffers may be used. For example, DNA may be eluted using the PURELINK™ Genomic Elution Buffer of the kit cited above from Invitrogen, which elution buffer contains Tris buffer, NaCl and EDTA. Alternatively, Tris buffer (10 mM Tris-HCl, pH 8.0-pH 9.0) or sterile water can be used in situations where EDTA inhibits downstream reactions.

For isolation of DNA from a microbiome containing sample, an optional step of removing RNA using a ribonuclease such as RNase A may be carried out. For isolation of RNA from a microbiome containing sample, an optional step of removing DNA using a deoxyribonuclease such as DNase I may be carried out.

Assays for purity: In addition to the efficiency of lysis, the purity of the nucleic acid can affect downstream analyses, as some methods carry over more and different interferents than others. Assays used to characterize DNA or RNA recovered from environmental and biological samples containing a microbiome population using protocols and reagents herein include the following. Yield of extracted DNA was determined using the NANODROP® ND1000 spectrophotometer (NanoDrop Technologies Inc., Wilmington, Del.) and the QUBIT™ dsDNA HS Assay Kit (Q32854) as well as the QUBIT™ dsDNA Br Assay Kit (Q32853) on the QUBIT™ Fluorometer (Invitrogen Co., Carlsbad, Calif.). As noted by the present inventors and others, for some samples, the spectrophotometer and the fluorometer do not give the same readings for yield of DNA. DNA concentration measured by the NANODROP® spectrophotometer has been observed to be typically somewhat higher than that measured by the QUBIT™ fluorometer. The QUBIT™ assay, specific to DNA, is considered to provide the more reliable concentration readout.

The A260/A280 nm ratio as well as an A260/A230 nm ratio are measures of purity; herein, the purity was determined using the NANODROP® ND1000 spectrophotometer (NanoDrop Technologies Inc., Wilmington, Del.), for example. Pure DNA has an A260/A280 nm ratio of 1.8, while pure RNA has an A260/280 ratio about 2.0. The A260/A230 nm ratio is a measure of contaminants that absorb at 230 nm; an expected A260/A230 nm ratio is 2.0-2.2 for each of RNA and RNA.

Integrity of DNA was determined by visualizing extracted DNA on a 0.8% agarose gel (w/v) containing EtBR electrophoresed in 1×TAE buffer (Thermo Fisher Scientific, Cat No. AM9869, diluted from 10×). Samples were loaded in a total volume of 20 microliters and normalized to allow for accurate comparisons between samples.

Isolated DNA may be amplified using PCR techniques, for example, including, but not limited, qPCR, digital PCR, hot start PCR, nested PCR, in situ polonony PCR, in situ rolling circle amplification (RCA), bridge PCR, picotiter PCR and emulsion PCR. Other suitable amplification methods include the ligase chain reaction (LCR), self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA).

Quantitative PCR was carried out for several microbial targets, including the genus *Bifidobacterium* (Gram positive), *Escherichia* (*E. coli*) (Gram negative), *Bacteroides/Prevotella* (Gram negative). An equal volume of DNA for all samples was used in the qPCR reaction with the TaqMan™ Universal Master Mix II, no UNG (Applied Biosystems Catalog No. #4440040) and custom TaqMan™ Assays were performed for detection of the targets. The sequences of the probes and primers are presented in Table 1.

TABLE 1

Sequences of TaqMan Primers/probes (5'-3'); SEQ ID NO's

| | |
|---|---|
| Bifidobacterium | Forward Primer: GCGTGCTTAACACATGCAAGTC-SEQ ID NO: 1<br>Reverse Primer: CATCCGGCATTACCACCCGTT-SEQ ID NO: 2<br>Probe: TCACGCATTACTCACCCGTTCGCC-SEQ ID NO: 3 |
| E. coli | Forward Primer: CATGCCGCGTGTATGAAGAA-SEQ ID NO: 4<br>Reverse Primer: CGGGTAACGTCAATGAGCAAA-SEQ ID NO: 5<br>Probe: TATTAACTTTACTCCCTTCCTCCCCGCTGAA-SEQ ID NO: 6 |
| Bacteroides/<br>Prevotella | Forward Primer: CCTACGATGGATAGGGGTT-SEQ ID NO: 7<br>Reverse Primer: CACGCTACTTGGCTGGTTCAG-SEQ ID NO: 8<br>Probe: AAGGTCCCCCACATTG-SEQ ID NO: 9 |

The qPCR reaction contained 2× MasterMix (5 μL), primer/probe (0.5 μL), DNA (2 μL), H$_2$O (2.5 μL) for a total volume of 10 μL. Cycling parameters for the 7900HT Fast Real-Time PCR system were 95° C. for 10 min; 95° C. for 15 s followed by 60° C. for 1 min×40.

Further master mixes for one-step and real time PCR reactions are the SYBR™ Green Master Mix and the Power SYBR™ Green Master Mix (Thermo Fisher Scientific Cat. No's. 4344463 and 4368577, respectively).

Isolated DNA may be characterized by sequencing at least a portion of the isolated DNA to generate resultant sequences. Microbiome sequencing can include one or more pre-amplification steps, library preparation, and sequencing using an NGS platform. Data analysis enables interpretations and conclusions to be made from the large amount of sequence data generated.

In one embodiment, the biological sample is a stool sample and the method further comprises comparing resultant sequences with a control set of sequences representing a healthy microbiome, thereby determining suitability of the stool sample for transplantation into a patient in need of a healthy gut microbiome. Characterization as a "normal" or "healthy" human stool sample can be determined, e.g., by methods in, U.S. Patent Publication No. 20140363400 to Jones et al. filed Aug. 15, 2014. A 16s ribosomal DNA analysis of isolated DNA from a microbiome sample is able to provide identification of the microbial genera represented by that microbiome sample and the level of each genera present, thereby providing a measure of the microbial diversity present and whether that diversity and level are consistent with normal feces and therefore suitable for viability tests and subsequent transplant.

In another embodiment, the biological sample is a forensic sample and the method further comprises comparing resultant sequences with a control set of sequences representing a forensic data set, thereby identifying a source of the sample. Resultant sequences may inform other aspects of a forensic sample, such as degree of decay or time of death, for example.

Isolated RNA may be characterized by the same methods as for DNA once the RNA is reverse transcribed using a polymerase having reverse transcriptase activity, or an enzymatically active fragment or mutant thereof. Exemplary reverse transcriptases include SUPERSCRIPT™ IV Reverse Transcriptase, SUPERSCRIPT™ III Reverse Transcriptase, M-MLV Reverse Transcriptase, ARRAYSCRIPT™ Reverse Transcriptase, all available from Thermo Fisher Scientific, Inc.

Exemplary Protocol for Stool: The content of stool samples is highly variable between donors as well as between samples for an individual donor depending on diet, use of probiotics, antibiotics and other factors. This variability is reflected in the total microbial DNA recovery, the representation of microbial species in the sample, and the presence and amount of miscellaneous interferents. As compared to results from typical laboratory or clinical samples, stool sample content is substantially more variable and thus error bars are typically larger.

An exemplary protocol utilized herein for generating a DNA containing solution having reduced amounts of interfering substances from stool is as follows. Stool samples were thoroughly mixed to generate a homogenous sample before weighing and transferring a portion to a bead tube. A Corning™ Microspatula (Corning, Cat No. 3013) is sufficiently sturdy for sample mixing and fits the opening of the bead tube.

a. Sample and Lysis Buffer (S1) are added to a bead tube in an amount according to the sample source: for human stool, use 0.2±0.05 g stool and ~600 μL of 51; for small animal stool, use 0.1±0.05 g stool and ~700 μL of 51. (The total volume is brought to 800 μL with 51.) The tube is capped securely, then vortexed to ensure that the sample is thoroughly dispersed in the liquid.

b. Lysis Enhancer (S2), 100 μL, is added to the tube and the tube is vortexed briefly, then incubated at 65° C. for 10 minutes. The tube is then homogenized by bead beating for 10 minutes at maximum speed on the vortex mixer using a hands-free adapter cited above and with horizontal agitation. After centrifugation at 14,000×g for 5 minutes, up to 400 μL of the supernatant is transferred to a clean microcentrifuge tube while avoiding any layer of debris that may be present on top of the bead pellet. This supernatant is referred to as a volume portion of lysate supernatant.

c. Interferent Depletion or Removal: Interferent Depleting Buffer (S3), 250 μL, is added to the 400 μL volume of supernatant from step b and the tube is vortexed immediately. Interferent Depleting Buffer comprises a solution of ammonium acetate and a flocculant in substantially equimolar concentrations. This single precipitation step removes substances that interfere with subsequent analysis of DNA and can, optionally, be carried out on ice for 5-10 minutes. After centrifugation at 14,000×g for 2 minutes, up to 500 μL of the supernatant is transferred to a clean 2-mL microcentrifuge tube, avoiding the pellet and any debris. This supernatant is referred to as a DNA-containing, interferent-depleted solution, i.e., materials that would interfere with later DNA analyses have been removed by precipitation using the Interferent Depleting Buffer.

DNA from the interferent-depleted solution is bound to a column as follows.

a. Binding Buffer (S4), 900 µL, is added to the interferent-depleted solution from step c above and the tube is vortexed briefly.
b. The mixture (700 µL from step a above) is loaded onto a spin column-tube assembly and centrifuged at 14,000×g for 1 minute. The flow-through is discarded and this step repeated with any remaining mixture.

Column-bound DNA is washed and eluted as follows.

a. The spin column is placed into a clean collection tube, 500 µL of Wash Buffer (S5 containing ethanol) is added and the spin column-tube assembly centrifuged at 14,000×g for 1 minute. The flow-through is discarded and the centrifugation is repeated.
b. The spin column from step a is placed in a clean tube, Elution Buffer (S6), 100 µL, is added and incubated at room temperature for one minute. The assembly is centrifuged at 14,000×g for one minute and the column is discarded. Purified DNA is in the eluate in the tube and is ready for immediate use in, e.g., downstream PCR, qPCR, sequencing or other applications.

Results herein demonstrate that a single solution of the two components together, i.e., a solution of ammonium acetate and a flocculant, e.g., aluminum ammonium sulfate dodecahydrate, added to the lysate supernatant in one step followed by centrifugation provided superior yield and purity of DNA as compared with using the two components sequentially as described in the '548 patent. For the data of the drawings, the final interferent removal conditions tested were (after addition of interferent removal reagent to lysate, volume portion thereof, supernatant thereof, or volume portion of supernatant thereof): a) 25 mM ammonium acetate; b) 50 mM ammonium acetate; c) 25 mM flocculant; d) 50 mM flocculant; e) 25 mM ammonium acetate; f) a solution of 25 mM ammonium acetate and 25 mM flocculant; g) a solution of 50 mM ammonium acetate and 50 mM flocculant; h) 25 mM ammonium acetate, then subsequent treatment with 25 mM flocculant; and i) 25 mM flocculant, then subsequent treatment with 25 mM ammonium acetate.

Analyses of DNA isolated from a human stool sample are shown in FIG. 1A (Sample 1, Donor 1), the isolation carried out under interferent-removal conditions a)-i) described above and following the exemplary protocol. Results are presented as concentration of DNA using Nanodrop analysis (▒), Qubit analysis (\\\\), and as purity of DNA using a 260/280 ratio (▲) and a 260/230 ratio (♦). By comparing the results of conditions a)-i), one can see that condition in which the ammonium acetate and flocculant were used together provided greater yield and purity than other conditions tested, including condition h) and i) in which the components were used sequentially, in each possible order. Note that the 260/280 and 260/230 ratios are particularly unreliable for samples with low DNA concentration (<5 ng/µL).

The average cycle threshold (Avg. $C_T$) levels of DNA isolated using Sample 1 and interferent-removal conditions a)-i) are provided in FIG. 1B for detection of each of three different bacterial targets: left set, gram positive *Bifidobacterium* (////); center set, gram negative *Escherichia coli* (▒); and right set, gram negative *Bacteroides/Prevotella* (////). The $C_T$ level is relative measure of the concentration of target in the PCR reaction and is a greater number when less template is present or when greater concentrations of interferent are present, therefore a lower $C_T$ level demonstrates a higher concentration of template present or a lower concentration of interferents present. A difference of one $C_T$ unit represents a two-fold difference in copy number. Condition f) consistently provided the lowest $C_T$ value for each type of microbe species tested. The agarose gel results of FIG. 1C confirms that condition f) provides the greatest yield of DNA as compared to remaining conditions tested.

The data of FIG. 2A, FIG. 2B and FIG. 2C provide similar analyses as for that of FIG. 1A-FIG. 1C for DNA isolated from a stool sample of a second human (Sample 2, Donor 2), the isolation carried out under interferent-removal conditions a)-i) as described above and following the exemplary protocol. A comparison of the data of FIG. 1A-FIG. 1C with that of FIG. 2A-FIG. 2C demonstrates that for different donors the effects of varying the concentration of ammonium acetate and flocculant were somewhat different. In condition g) for this donor 2, the solution of ammonium acetate and flocculant was used in one step and the concentration of each is 2-fold that of condition f). This result is due to substantial variation of each individual's GI tract microbiome, and any presence of blood, bile, and/or food debris and fiber. In this work, it has been observed that stool from donors who consume more fruits and vegetables represents a greater challenge for removal of interferents as compared to stool from donors who are meat eaters. Different formulations appear to be more effective than others for removal of some subsets of PCR inhibitors. However, the technology herein provides the most efficient and effective formulation for successful isolation of interferent-depleted DNA from stool samples regardless of diet.

Direct comparison of present reagents and methods with the PowerSoil® DNA Isolation Kit reagents and methods: An unexpected finding herein that a solution of ammonium acetate and flocculant together in one interferent removal step provided more effective isolation of DNA than sequential use of the ammonium acetate and flocculant was confirmed by direct side-by-side comparison of the present protocol with the kit protocol and reagents of the PowerSoil® DNA Isolation Kit as purchased from Mo Bio Laboratories. To ensure an accurate comparison between the two, a heat step (65° C. for 10 minutes) was added prior to step one of the PowerSoil® Kit protocol. Three different users carried out the comparisons by each isolating DNA from three different donors, (Donors 3-5 for User 1; Donors 6-8 for User 2; and Donors 9-11 for User 3). Data are provided in FIG. 3A-FIG. 3C for User 1, FIG. 4A-FIG. 4C for User 2, and FIG. 5A-FIG. 5C for User 3.

For User 1, the A260/A280 and A260/A230 nm ratios for the data of FIG. 3A are as follows. The samples were run in triplicate.

| Donor | Isolation Kit* | A260/A280 | A260/A230 |
| --- | --- | --- | --- |
| Donor 3 | PL | 1.86 | 1.67 |
|  |  | 1.87 | 2.02 |
|  |  | 1.87 | 1.93 |
|  | MB | 1.7 | 1.41 |
|  |  | 1.78 | 2.01 |
|  |  | 1.7 | 1.35 |
| Donor 4 | PL | 1.87 | 1.86 |
|  |  | 1.8 | 1.63 |
|  |  | 1.84 | 1.8 |
|  | MB | 1.65 | 1.07 |
|  |  | 1.7 | 1.47 |
|  |  | 1.77 | 1.22 |
| Donor 5 | PL | 1.8 | 1.98 |
|  |  | 1.91 | 2.15 |
|  |  | 1.83 | 1.83 |
|  | MB | 1.63 | 1.4 |
|  |  | 1.87 | 1.66 |
|  |  | 1.37 | 0.98 |

*PL refers to the purification procedure described herein; MB refers to the PowerSoil® Kit protocol For User 3, the A260/A280 and A260/230 nm ratios for the data of FIG. 5A are as follows. The samples were run in triplicate.

| Donor | Isolation Kit* | A260/A280 | A260/A230 |
|---|---|---|---|
| Donor 9 | PL | 1.9 | 2.08 |
| | | 1.92 | 1.87 |
| | | 1.92 | 2.2 |
| | MB | 1.72 | 0.93 |
| | | 1.85 | 1.64 |
| | | 1.78 | 1.1 |
| Donor 10 | PL | 1.88 | 1.81 |
| | | 1.85 | 1.71 |
| | | 1.87 | 1.99 |
| | MB | 1.89 | 1.95 |
| | | 1.86 | 2.65 |
| | | 1.93 | 2.18 |
| Donor 11 | PL | 1.78 | 1.45 |
| | | 1.81 | 1.39 |
| | | 1.77 | 1.17 |
| | MB | 1.57 | 0.86 |
| | | 1.69 | 1.05 |
| | | 1.68 | 1.22 |

A review of the data of FIG. 3A-FIG. 3C for User 1, FIG. 4A-FIG. 4C for User 2, and FIG. 5A-FIG. 5C for User 3 shows that the herein described reagents and protocol provide fast and reliable purification of microbial and host DNA from stool, outperforming the PowerSoil® DNA Isolation Kit in the parameters of DNA yield, purity, gel appearance, and PCR amplification results. The workflow is shorter. The interferent removal reagent described herein provides very efficient depletion of enzymatic inhibitors from stool sample lysate supernatants, in one fast and easy step.

Sequencing analysis of DNA isolated from human stool as described herein revealed the dominant presence of the bacterial genera cited in FIG. 6. The sequencing was carried out by Diversigen (Houston Tex.) using 16S rDNA gene sequencing as follows. The 16S rDNA V4 region was amplified by PCR and sequenced in the MISEQ platform (Illumina, San Diego, Calif.) using the 2×250 bp paired-end protocol yielding pair-end reads that overlap almost completely. The primers used for amplification contain adapters for MISEQ sequencing and single-end barcodes allowing pooling and direct sequencing of PCR products (Caporaso et al. *The ISME Journal* 2012; 6(8): 1621-4).

The 16S rRNA gene pipeline data incorporates phylogenetic and alignment-based approaches to maximize data resolution. The read pairs were de-multiplexed based on the unique molecular barcodes, and reads were merged using USEARCH v7.0.1090 (Edgar R. C., *Bioinformatics* 2010; 26(19): 2460-1; Caporaso J. G., *Nature Methods* 2010; 7(5): 335-6), allowing zero mismatches and a minimum overlap of 50 bases. Merged reads are trimmed at first base with Q5. In addition, a quality filter was applied to the resulting merged reads and reads containing above 0.05 expected errors were discarded.

16S rRNA gene sequences were clustered into Operational Taxonomic Units (OTUs) at a similarity cutoff value of 97% using the UPARSE algorithm. OTUs were mapped to an optimized version of the SILVA Database (Edgar 2013 *Nature Methods* 10 (10): 996-8; Quast, C. et al. 2013 *Nucleic Acids Res* 41(Database issue): D590-596) containing only the 16S v4 region to determine taxonomies. Abundances were recovered by mapping the de-multiplexed reads to the UPARSE OTUs. A custom script constructed a rarefied OTU table from the output files generated in the previous two steps for downstream analyses of alpha-diversity, beta-diversity (Lozupone, C. et al. 2005 *Appl Environ Microbiol* 71(12): 8228-8235), and phylogenetic trends.

Samples from two donors (D12, D13) were processed in triplicate as described above. Donor 12 has a diet high in meat, while Donor 13 has a diet high in plants. The top bacterial genera are shown as percentage of total reads. At the genus level, both donors were found to have the highest representation of *Bacteroides* (over 20% for both) and *Faecalibacterium* (over 20% for both). However, for many types of bacteria, substantial differences between the donors were observed.

The following bacteria were present at substantially higher levels in Donor 12 (the meat eater): Sutterella (5.3-7% vs<0.1% D13); *Coprococcus* (2.4-3.5% vs 0.2-0.4% D13); *Streptococcus* (1.6-2.2% vs 0.1% D13); and *Clostridium* (2-2.8% vs 0.3% D13).

The following bacteria were present at substantially higher levels in Donor 13 (the plant eater): *Roseburia* (1.1-1.3% vs 0.3-0.5% D12); *Lachnospira* (4.2-5.5% vs 2-3.4% D12); *Subdoligranulum* (2.7-3.9% vs<0.1% D12); *Ruminococcus* (2-2.3% vs<0.1% D12); and *Pseudobutyrivibrio* (13.6-21.4% vs 5.5-6.2% D12).

The substantial differences observed between the stool microbiome communities of the two donors are largely explained by differences in their diet. However it should be noted that microbiome is also affected by many other factors such as the environment, health state, uptake of antibiotics and probiotics, and age. The health aspect is extremely important, as the microbiome seems to influence (or at least is associated with) multiple diseases, including inflammatory bowel disease, malnutrition, celiac disease, obesity, vaginosis, asthma, diabetes, cancer, pancreatic disease, allergies, neurological disorders, and heart disease. Thus, in addition to the fundamental research aimed at understanding the composition and functions of the microbiome community, the immediate practical application for the above described workflows is diagnostics, monitoring efficiency of the treatments, and detection of pathogens.

DNA was also isolated from samples of rat stool (one pellet, 0.1-0.15 g) from three donor rats, each carried out in triplicate. The yield and variability of microbial and host DNA from each donor is shown in FIG. 7. The interferent removal reagent was a solution of 50 mM ammonium acetate, 65 mM aluminum ammonium sulfate dodecahydrate and the protocol followed is described above for small animal stool samples. No ice incubation was carried out and the interferents were precipitated by centrifugation immediately after addition of the reagent and brief vortexing.

Exemplary protocol for soil samples: The protocol for isolating microbial DNA from soil is the same as that for a large animal stool sample. FIG. 8 provides plots of DNA yield from three samples of soil (0.2+/−0.05 g input), each carried out in triplicate. The interferent removal reagent was a solution of 50 mM ammonium acetate, 65 mM aluminum ammonium sulfate dodecahydrate. Incubation on ice for ten minutes was carried out after addition of the interferent removal reagent and brief vortexing; the interferents were removed by centrifugation. Soil sample #1 was collected from a dry, sunny location and had a "chalky" appearance. Soil sample #2 was rich garden soil and soil sample #3 was from a muddy garden.

Therefore, the compositions and methods as provided herein allow for isolation of substantial amounts of interferent-free DNA from biological samples such as human stool as well as from rat stool. Further, the compositions and methods as provided herein allow for isolation of substantial amounts of interferent-free DNA from environmental samples such as soil samples. The compositions and methods presented herein provide for efficient and effective depletion of interferents that differ in nature, size and charge, without compromising nucleic acid yield and while maintaining a reasonably short and convenient workflow.

The compositions, methods, and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

Although the disclosed teachings have been described with reference to various applications, methods, and compositions, it will be appreciated that various changes and modifications can be made without departing from the teachings herein. The foregoing examples are provided to better illustrate the present teachings and are not intended to limit the scope of the teachings herein. Certain aspects of the present teachings can be further understood in light of the following claims.

What is claimed is:

1. A method for isolating a nucleic acid from an environmental or biological sample comprising the nucleic acid and at least one nucleic acid analysis-interferent, the method comprising:
   a. disrupting the sample using chemical treatment and heat treatment, followed by mechanical agitation, to produce a lysate; and
   b. contacting the lysate, a volume portion thereof, a supernatant thereof, or a volume portion of supernatant thereof, with a composition comprising a substantially equimolar concentration of ammonium acetate and aluminum ammonium sulfate dodecahydrate, to form an interferent-containing precipitate and a nucleic acid-containing, interferent-depleted solution; and
   c. isolating nucleic acid from the nucleic acid-containing interferent-depleted solution to form isolated nucleic acid,
wherein the environmental or biological sample comprises a soil sample or a stool sample.

2. The method of claim 1 wherein the chemical treatment comprises contacting the sample with a lysis reagent comprising at least one chaotropic agent, wherein the lysis reagent does not contain ammonium acetate, sodium chloride, ammonium sulfate, potassium acetate or sodium acetate.

3. The method of claim 2 wherein the lysis reagent does not contain a detergent.

4. The method of claim 1 wherein the composition comprises a solution of 5 mM to 200 mM ammonium acetate and 5 mM to 200 mM aluminum ammonium sulfate dodecahydrate.

5. The method of claim 4 wherein the composition comprises a solution of 50 mM to 130 mM ammonium acetate and 50 mM to 130 mM aluminum ammonium sulfate dodecahydrate.

6. The method of claim 1 wherein the environmental or biological sample comprises a sample derived from an animal, food, a plant or a component thereof, soil, sediment, sludge, compost, decomposing biological matter, a biopsy, a histological sample, a body fluid or swab thereof, hair, a skin sample or swab thereof, a fecal sample or swab thereof, archaeological remains, a peat bog, a water filter or swab thereof, terrestrial water, subterranean water, industrial water or filter thereof, a dust filter or swab thereof, transport media, culture media, or an air filter or swab thereof.

7. The method of claim 1 wherein the nucleic acid comprises DNA and the method further comprises contacting the isolated DNA with an enzyme utilizing DNA as a substrate, wherein the enzyme is a polymerase, a ligase, a phosphatase, or an enzymatically active fragment or mutant thereof.

8. The method of claim 1 wherein the nucleic acid comprises DNA and the method further comprises characterizing the isolated DNA by sequencing at least a portion of the DNA.

9. The method of claim 8 wherein the biological sample is a stool sample and the method further comprises comparing resultant sequences with a control set of sequences representing a healthy microbiome, thereby determining suitability of the stool sample for transplantation into a patient in need of a healthy gut microbiome, or determining presence of abnormal cells in the sample indicative of cancer.

10. The method of claim 8 further comprising comparing resultant sequences with a control set of sequences representing a forensic data set, thereby identifying a source of the sample, or degree of decay of a host source of the sample.

11. The method of claim 1 wherein the environmental or biological sample comprises a soil sample or a stool sample.

12. The method of claim 1 wherein the biological sample is a stool sample and wherein the isolated DNA is assayed for DNA characteristic of a pathogenic organism.

13. The method of claim 12 wherein the pathogenic organism is *C. difficile* or methicillin-resistant *Staphylococcus aureus*.

14. The method of claim 1 wherein the nucleic acid is RNA, the method comprising:
contacting the sample with a RNA stabilization reagent prior to the disrupting step.

15. The method of claim 1 wherein the heat treatment comprises heating to 65° C. to 95° C. for 5 to 10 minutes.

16. The method of claim 1 wherein the sample is subjected to chemical treatment, followed by heat treatment, and then subjected to mechanical agitation to produce the lysate.

17. The method of claim 1, wherein the mechanical agitation comprises bead beating and/or homogenization.

18. A method for isolating a nucleic acid from an environmental or biological sample comprising the nucleic acid and at least one nucleic acid analysis-interferent, the method comprising:
a. disrupting the sample using mechanical agitation, enzymatic treatment, chemical treatment, heat treatment, or a combination thereof to produce a lysate; and
b. contacting the lysate, a volume portion thereof, a supernatant thereof, or a volume portion of supernatant thereof, with a composition comprising a substantially equimolar concentration of ammonium acetate and aluminum ammonium sulfate dodecahydrate, to form an interferent-containing precipitate and a nucleic acid-containing, interferent-depleted solution; and
c. isolating nucleic acid from the nucleic acid-containing interferent-depleted solution to form isolated nucleic acid,
wherein the environmental or biological sample comprises a soil sample or a stool sample.

19. A method for isolating a nucleic acid from an environmental or biological sample comprising the nucleic acid and at least one nucleic acid analysis-interferent, the method comprising:
a. disrupting the sample using mechanical agitation, enzymatic treatment, chemical treatment, heat treatment, or a combination thereof to produce a lysate; and
b. contacting the lysate, a volume portion thereof, a supernatant thereof, or a volume portion of supernatant thereof, with a composition comprising a substantially equimolar concentration of ammonium acetate and aluminum ammonium sulfate dodecahydrate, to form an interferent-containing precipitate and a nucleic acid-containing, interferent-depleted solution; and
c. isolating nucleic acid from the nucleic acid-containing interferent-depleted solution to form isolated nucleic acid.

* * * * *